(12) United States Patent
Pedersen et al.

(10) Patent No.: US 8,323,971 B2
(45) Date of Patent: Dec. 4, 2012

(54) DIFFERENTIATION OF PLURIPOTENT CELLS INTO PRIMARY GERM LAYER PROGENITORS

(75) Inventors: Roger Pedersen, Cambridge (GB); Ludovic Vallier, Cambridge (GB)

(73) Assignee: Cambridge Enterprise Limited (GB)

( * ) Notice: Subject to any disclaimer, the term of this patent is extended or adjusted under 35 U.S.C. 154(b) by 495 days.

(21) Appl. No.: 12/514,178

(22) PCT Filed: Nov. 9, 2007

(86) PCT No.: PCT/GB2007/004291
§ 371 (c)(1),
(2), (4) Date: May 8, 2009

(87) PCT Pub. No.: WO2008/056166
PCT Pub. Date: May 15, 2008

(65) Prior Publication Data
US 2010/0034785 A1    Feb. 11, 2010

(30) Foreign Application Priority Data
Nov. 9, 2006 (GB) .................................. 0622394.5

(51) Int. Cl.
*C12N 5/00* (2006.01)
*C12N 5/02* (2006.01)

(52) U.S. Cl. .................. 435/377; 435/375; 435/325

(58) Field of Classification Search ................ 435/377, 435/375, 325
See application file for complete search history.

(56) References Cited

U.S. PATENT DOCUMENTS 7,045,353 B2 * 5/2006 Benvenisty .................... 435/377
7,442,548 B2 * 10/2008 Thomson et al. ............. 435/377
2005/0095708 A1 * 5/2005 Pera et al. ..................... 435/369
2005/0196864 A1 * 9/2005 Goldman et al. ............. 435/456
2005/0208021 A1 * 9/2005 Calos ........................... 424/93.2

FOREIGN PATENT DOCUMENTS

| EP | 1 302 536 A2 | 4/2003 |
| WO | WO 2006/029198 A2 | 3/2006 |
| WO | WO 2007/148098 A2 | 12/2007 |

OTHER PUBLICATIONS

Schuldiner et al. PNAS 97(21):11307-11312, 2000.*
Klimanskaya Irina et al., "Human Ebryonic Stem Cells Derived Without Feeder Cells", *Lancet*, 365(9471), 1636-1641 (May 7, 2005).
Ludwig T E et al., "Derivation of human embryonic stem cells in defined conditions" *Nature Biotechnology*, 24(2), 185-187 (Feb. 1, 2006).
Schatten Gerald et al., "Culture of human embryonic stem cells", *Nature Methods*, 2(6), 455-463 (Jun. 2005).
Vallier L et al., "Activin/Nodal and FGF pathways cooperate to maintain pluripotency of human embryonic stem cells", *Journal of Cell Science*, 118(19), 4495-4509 (Oct. 1, 2005).
Vallier L et al., "Nodal inhibits differentiation of human embryonic stem cells along the neuroectodermal default pathways", *Developmental Biology*, 275(2), 403-421 (Nov. 15, 2004).
PCT/GB2007/004291 International Search Report and Written Opinion, dated May 26, 2008, 16 pages.

* cited by examiner

*Primary Examiner* — Marcia S Noble
(74) *Attorney, Agent, or Firm* — Choate Hall & Stewart LLP

(57) ABSTRACT

This invention relates to the culture of pluripotent cells in a fully humanised chemically defined medium. Cells may be cultured over a prolonged period of time without losing their pluripotent status or may be controllably induced to differentiate into progenitor cells of the three primary germ layers by the addition of differentiation factors, for example differentiation factors which modulate one or more of the Activin/Nodal, FGF, Wnt or BMP signalling pathways.

17 Claims, 8 Drawing Sheets

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 1
ctgtgacagg atggtgatac                                              20

<210> SEQ ID NO 2
<211> LENGTH: 20
<212> TYPE: DNA
```

-continued

```
<213> ORGANISM: Artificial sequence
<220> FEATURE:
<223> OTHER INFORMATION: Synthetic sequence: Primer

<400> SEQUENCE: 2
atggtgcagg gtagtagatg                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 3
ggagatgtac ctggacctgc                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 4
catctgaggc gcagctacag                                              20
```

DIFFERENTIATION OF PLURIPOTENT CELLS INTO PRIMARY GERM LAYER PROGENITORS

This invention relates to the differentiation of human pluripotent cells, such as embryonic stem cells (hESCs), into progenitor cells of the primary germ layers.

Human Embryonic Stem cells (hESCs) are pluripotent cells derived from embryos cultured from the blastocyst stage. Their embryonic origin confers on them the capacity to differentiate into all cell types of the body, thus providing compelling new opportunities for regenerative medicine and for studying mechanisms of early human cell fate commitment. Generation of fully functional cell types from hESCs is still a major challenge with few studies demonstrating unambiguously the preservation of the properties characterising their counterpart produced during normal development. Modelling in vitro the early step of early development may nevertheless provide the best approach for generating in vitro progeny with native properties. The first event of differentiation during mammalian development is the specification of the extra-embryonic tissues starting at the morula with the trophectoderm from which the placenta originates. Primitive endoderm is formed at the late blastocyst stage and differentiates into parietal and visceral endoderm during implantation.

Differentiation of the three primary germ layers mesoderm, endoderm and ectoderm, during gastrulation establishes the precursor population for all the adult tissues. Muscles, heart, kidney, vascular and haematopoietic system arise from the mesoderm, the nervous system and the epidermis from ectoderm and the pancreas, lungs, gut, and thyroid from the endoderm. Therefore, the generation of endoderm, mesoderm, and ectoderm progenitors is a key step toward the generation of fully differentiated clinically useful cell types from hESCs. Several methods with variable efficiency are currently available to generate such cells from hESCs. However, those studies are strictly focused on a specific primary germ layer and they cannot be used for multi-lineage differentiation of hESCs. More importantly, they used media containing Foetal Bovine Serum (FBS), mouse feeders, and undefined cellular matrix which limit the potential of their interest concerning clinical applications. The presence of undefined factors also limits their application as in vitro model of differentiation to study early mammalian development.

The present inventors have discovered that human pluripotent cells can be grown in a fully humanised chemically defined medium over a prolonged period of time without losing their pluripotent status and, furthermore, can be induced by the addition of differentiation factors, to controllably differentiate in this medium into progenitor cells of the three primary germ layers.

An aspect of the invention provides a method of producing a population of partially differentiated progenitor cells comprising;
  culturing human pluripotent cells in a humanised chemically defined medium (CDM) supplemented with one or more differentiation factors, and,
  allowing said pluripotent cells to differentiate into progenitor cells.

A partially differentiated progenitor is a daughter or descendant of a undifferentiated stem cell, with a more committed phenotype and/or a more reduced differentiation potential compared to the original stem cell. Partially differentiated progenitor cells are committed to a lineage in one of the three primary germ layers and are capable of giving rise to a plurality of distinct phenotypes e.g. an ectoderm progenitor is able to differentiate under appropriate conditions into all cell types in the epidermis and the nervous system including neurons with different neurotransmitter subtypes, astrocytes, and oligodendrocytes, a mesoderm progenitor is able to differentiate under appropriate conditions into all cell types in the muscles, heart, kidney, vascular and haematopoietic systems and an endoderm progenitor is able to differentiate under appropriate conditions into all cell types in the pancreas, lungs, gut, and thyroid. Partially differentiated progenitor cells also include mesendoderm progenitor cells, which can further differentiate into either mesoderm or endoderm progenitors. Mesendoderm progenitor cells may also be termed mesoderm/endoderm progenitors.

Culturing of the human pluripotent cells in a humanised chemically defined medium (CDM) supplemented with one or more differentiation factors as described herein induces the pluripotent cells to differentiate into progenitor cells.

Partially differentiated progenitor cells produced by the present methods may be substantially free from other cell types. In some embodiments, progenitor cells may be separated from other cell types using any technique known to those skilled in the art, including those based on the recognition of extracellular epitopes by antibodies and magnetic beads or fluorescence activated cell sorting (FACS) including the use of antibodies against extracellular regions of characteristic markers as described below.

Human pluripotent cells include embryonic stem cells, fetal and adult somatic stem cells or neural crest cells.

A human embryonic stem cell (hESC) is a cell derived from an early stage embryo, which exhibits an undifferentiated phenotype and is potentially pluripotent i.e. it is capable of giving rise to any cell type in an individual. An hESC may be a cell obtained from an embryo or may be a descendent of such a cell. Suitable hESCs cells may be obtained from a cultured hESC cell line, such as H9 or hSF-6. Further examples of suitable human embryonic stem cells are described in (Thomson J A et al Science 282: 1145-1147 (1998); Reubinoff et al. Nat 30 Biotechnol 18:399-404 (2000); Cowan, C. A. et al. N. Engl. J. Med. 350, 1353-1356 (2004), Gage, F. H., et al. Ann. Rev. Neurosci. 18 159-192 (1995); and Gotlieb (2002) Annu Rev. Neurosci 25 381-407); Carpenter et al. Stem Cells. 5 (1): 79-88 (2003); see also: the NIH stem cell registry on the world wide web at the hypertext protocol transfer address of "sterncells.nih.gov/research/registry/". Potentially clinical grade hESCs are described in Klimanskaya, I. et al. Lancet 365, 1636-1641 (2005), Ludwig, T. E. et al. Nat. Biotechnol. 24, 185-187 (2006).

In other embodiments, the human pluripotent cells are not hESCs, and may, for example, be fetal or adult somatic stem cells or neural crest cells.

A human pluripotent cell may express one or more of the following pluripotency associated markers: Oct4, Sox2, Alkaline Phosphatase, SSEA-3, Nanog, SSEA-4 and Tra-1-60. A human pluripotent cell may lack markers associated with specific differentiative fates, such as Bra, Sox17, FoxA2, αFP, Sox1, NCAM, GATA6, GATA4, Hand1 and CDX2.

A population of human pluripotent cells for use in the present methods may be obtained by culturing cells from a pluripotent cell line, for example an hESC cell line, using conventional techniques (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)) For example, human pluripotent cells suitable for use in the present methods may be conventionally cultured in a culture dish on a layer of feeder cells, such as irradiated mouse embryonic fibroblasts (MEF), at an appropriate density (e.g. $10^5$ to $10^6$ cells/60 mm dish), or on an appropriate substrate with feeder conditioned or defined medium. Human pluripotent cells for use in the present methods may be passaged by enzymatic or mechanical means. Suitable culture media for human pluripotent cells include Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human bFGF.

In preferred embodiments, a population of human pluripotent cells for use in the present methods may be obtained by culturing human pluripotent cells in humanised CDM comprising Activin and FGF2, as described below.

If a human embryo is used as a source of human pluripotent cells, the human embryo is one that would otherwise be destroyed without use, or stored indefinitely, especially a human embryo created for the purpose of IVF treatment for a couple having difficulty conceiving. IVF generally involves creation of human embryos in a number greater than the number used for implantation and ultimately pregnancy. Such spare embryos may commonly be destroyed. With appropriate consent from the people concerned, in particular the relevant egg donor and/or sperm donor, an embryo that would otherwise be destroyed can be used in an ethically positive way to the benefit of sufferers of severe degenerative disorders such as Parkinson's disease. Furthermore, ES cells may be derived from one embryo cell without destroying the whole embryo (Chung Y et al, Nature 2006; 439(7073):216-9.). The present invention itself does not concern the use of a human embryo in any stage of its development. As noted, the present invention minimizes the possible need to employ a material derived directly from a human embryo, whilst allowing for development of valuable therapies for common and devastating diseases. Any therapeutic interventions based on the present invention must also be performed according to the relevant national laws and ethical guidelines.

A human pluripotent cell suitable for use in the present methods may be substantially free from one or more other cell types. Human pluripotent cells may, for example, be separated from other cell types, using any technique known to those skilled in the art, including those based on the recognition of extracellular epitopes by antibodies and magnetic beads or fluorescence activated cell sorting (FACS) including the use of antibodies against extracellular regions of molecules found on stem cells such as SSEA4.

A chemically defined medium (CDM) is a nutritive solution for culturing cells which contains only specified components, preferably components of known chemical structure. A humanised chemically defined medium is devoid of components derived from non-human animals, such as Foetal Bovine Serum (FBS), Bovine Serum Albumin (BSA), and mouse feeder cells.

A suitable humanised chemically defined medium may comprise a basal culture medium, such as IMDM and/or F12 supplemented with insulin, for example at 0.5 μg/ml to 70 μg/ml, transferin, for example at a concentration of 1.5 μg/ml to 150 μg/ml, an antioxidant, such as 1-thiolglycerol, for example at a concentration of 45 μM to 4.5 mM, lipids, and one or more of human serum albumin, polyvinyl alcohol (PVA), Plasmanate™ (human albumin, alpha-globulin and beta globulin: Talecris Biotherapeutics NC USA) or Buminate™ (human albumin: Baxter Healthcare), for example at a concentration of 0.5 mg/ml to 50 mg/ml.

Suitable humanised CDM include humanised Johansson and Wiles CDM. Johansson and Wiles CDM is described in Johansson and Wiles (1995) Mol Cell Biol 15, 141-151. Humanised Johansson and Wiles CDM consists of: 50% IMDM (Gibco) plus 50% F12 NUT-MIX (Gibco); 7 μg/ml insulin; 15 μg/ml transferrin; 5 mg/ml human serum albumin, polyvinyl alcohol (PVA), Plasmanate™ or Buminate™; 1% chemically defined lipid concentrate (Invitrogen); and 450 μM 1-thiolglycerol.

Preferably, cells are harvested using collagenase-free reagents, for example Accutase™ (BioWest).

The humanised CDM may comprise one or more differentiation factors. Differentiation factors include growth factors which modulate one or more of the Activin/Nodal, FGF, Wnt or BMP signalling pathways. Examples of differentiation factors include FGF2, BMP4, retinoic acid, TGFbeta, GDF3, LIF, IL and activin.

Human pluripotent cells, such as hESCs, may be cultured in humanised CDM as described above using routine mammalian cell culture techniques, for example, human fibronectin coated plates may be employed. The culture of mammalian cells is well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430). Standard mammalian cell culture conditions may be employed, for example 37° C., 21% Oxygen, 5% Carbon Dioxide. Media is preferably changed every two days and cells allowed to settle by gravity.

In some embodiments, a population of ectoderm progenitor cells is produced using the differentiation factors FGF2 and an activin antagonist. Ectoderm progenitor cells may include neuroectoderm and epidermal progenitor cells. Preferably, the population of ectoderm progenitor cells is produced in the absence or substantial absence of Bone Morphogenetic Protein activity.

A method of producing a population of ectoderm progenitor cells may comprise;
  culturing hESCs in a humanised CDM supplemented with FGF2 and an activin antagonist, and,
  allowing said hESCs to differentiate into said progenitor cells.

The hESCs may be cultured in humanised CDM supplemented with FGF2 and an activin antagonist for 5 to 10 days.

Ectoderm progenitor cells express Sox2 in absence of Oct4. Ectoderm progenitor cells may also express NCAM and Nestin. In some embodiments, cells may differentiate into fully differentiated neuronal cells which express one or more of βIII-tubulin, Neurofilament, GFAP and Glutamate.

Human fibroblast growth factor 2(FGF2) (NCBI GeneID: 2247, nucleic acid sequence NM_002006.3 GI: 41352694, amino acid sequence NP_001997.4 GI: 41352695) may be produced using routine recombinant techniques or obtained from commercial suppliers (e.g. R&D, Minneapolis, Minn., USA). Conveniently, the concentration of FGF2 in the medium may be from 1 to 100 ng/ml, preferably about 12 ng/ml.

Activin A (NCBI GeneID: 3624 nucleic acid reference sequence NM_002192.2 GI: 62953137, amino acid reference sequence NP_002183.1 GI: 4504699) is a dimeric polypeptide which exerts a range of cellular effects via stimulation of the Activin/Nodal pathway.

A number of antagonists of Activin are known, including SB431542 (4-(5-Benzol[1,3]dioxol-5-yl-4-pyrldin-2-yl-1H- imidazol-2-yl)-benzamide hydrate; Sigma, Tocris Bioscience, Bristol UK) and a soluble protein factor, such as lefty (e.g. human lefty 2: NP_003231.2 GI:27436881), cerberus (e.g. human Cerberus 1: NP_005445.1 GI:4885135) or follistatin (e.g. human foistatin: NP_006341.1 GI:5453652). Conveniently, the concentration of antagonist in the medium may be from 1 to 100 µM, preferably about 10 µM.

The ectoderm progenitor cells produced by the above method may be isolated and/or purified using any suitable method, for example FACS.

The ectoderm progenitor cells may, for example, be expanded or propagated in culture or used in clinical applications as described below. In some embodiments, progenitor cells may be further differentiated. For example, colonies of progenitor cells may be detached from plates, and grown in CDM under non-adherent conditions to generate embryoid bodies (EBs). The EBs may then be grown under adherent conditions, for example on fibronectin coated plates to produce neuronal outgrowths comprising fully differentiated neuronal cells.

In other embodiments, a population of mesendoderm progenitor cells is produced using the differentiation factors are Activin, FGF2 and BMP4 and the CDM-PVA medium. Mesendoderm progenitor cells may be endoderm or mesoderm progenitor cells.

A method of producing a population of mesendoderm progenitor cells may comprise;
culturing human pluripotent cells in humanised CDM-PVA comprising activin, FGF2 and BMP4, and,
allowing said human pluripotent cells to differentiate into said progenitor cells.

Humanised CDM-PVA is humanised chemically defined medium comprising 5 mg/ml polyvinyl alcohol (PVA) instead of human serum albumin.

Mesendoderm (i.e. mesoderm/endoderm) progenitor cells may be endoderm progenitors which express Sox17 and CXCR4 and the mesendoderm marker or mesoderm progenitors which express one or more of Brachyury, Goosecoid, Mixl1, GATA6 and PDGFαR.

Humanised CDM for inducing mesendoderm differentiation may comprise from 1 to 100 ng/ml of BMP4, preferably about 10 ng/ml. BMP4 (MIM: 112262 NCBI GeneID: 652 reference amino acid sequence NP_001193.1 GI: 4502423, reference nucleotide sequence NM_001202.2 GI: 19528648) may be produced by conventional recombinant techniques or obtained from commercial suppliers (e.g. R&D Systems Inc MN USA).

Humanised CDM for inducing mesendoderm differentiation may comprise from 1 to 200 ng/ml of activin A. Activin A is described in more detail above. The proportion of endoderm progenitors in the mesendoderm progenitor population may be increased by increasing the concentration of activin A. For example, a population of endoderm progenitors may be produced by employing greater than 50 ng/ml activin A, for example about 100 ng/ml. The proportion of mesoderm progenitors in the mesendoderm progenitor population may be increased by decreasing the concentration of activin A. For example, a population of mesoderm progenitors may be produced by employing less than 50 ng/ml activin A, for example, about 30 ng/ml. In some embodiments, the level of activin A may be reduced to lower levels, for example, less than 30 ng/ml, less than 20 ng/ml, less than 10 ng/ml, zero or substantially zero, to produce a mesoderm progenitor population.

The humanised CDM may comprise from 1 to 100 ng/ml of FGF2, preferably about 20 ng/ml. FGF2 is described in more detail above.

In some embodiments, humanised CDM for producing a population of mesendoderm progenitor cells may further comprise a phosphatidylinositol 3-kinase inhibitor, such as LY294002 (Maclean et al (2007) *Stem Cells* 25 29-38).

Mesoderm and endoderm (i.e. mesendoderm) progenitor cells may be isolated and/or purified using any suitable method, for example FACS.

In preferred embodiments, human pluripotent cells for use in the methods described above are subjected to two preliminary treatment steps.

In a first preliminary step, the cells may be cultured in CDM-PVA supplemented with activin and FGF2, for example for 1 to 4 days, preferably about 2 days. Typically, 5 to 20 ng/ml of activin A, preferably about 10 ng/ml, and 1 to song/ml of FGF2, preferably about 12 ng/ml, may be employed.

In a second preliminary step, the cells may then be cultured for 1-5 days in humanised CDM-PVA comprising an FGF2 antagonist and a low concentration of activin. Typically, 1 to 50 µM of the FGF2 antagonist, preferably about 10 µM, and 1 to 10 ng/ml activin, preferably about 5 ng/ml, may be employed.

Suitable FGF2 antagonists include 3-[3-(2-Carboxyethyl)-4-methylpyrrol-2-methylidenyl]-2-indolinone (SU5402). SU5402 may be conveniently obtained from commercial suppliers (e.g. Calbiochem).

The resultant cells may then be cultured in humanised CDM comprising Activin, FGF2 and BMP4 as described above and allowed to differentiate into mesoendoderm cells.

A method of producing a population of mesendoderm progenitor cells may thus comprise;
(i) culturing human pluripotent cells in humanised CDM-PVA supplemented with activin and FGF2,
(ii) further culturing said cells in humanised CDM-PVA supplemented with an FGF2 antagonist and activin,
(iii) further culturing said cells in humanised CDM-PVA supplemented with FGF2, BMP4 and activin, and
allowing said cells to differentiate into said mesendoderm progenitor cells.

The concentration of activin in step (ii) may be reduced relative to the concentration of activin in step (i). The concentration of activin in step (iii) may be varied to alter the proportion of mesoderm and endoderm cells in the population, as described above.

The population of mesendoderm progenitor cells may be allowed to differentiate further In other embodiments, a population of extra-embryonic progenitor cells cells is produced using BMP4 and humanised CDM.

A method of producing a population of extra-embryonic progenitor cells may comprise;
culturing human pluripotent cells in humanised CDM comprising BMP4, and,
allowing said human pluripotent cells to differentiate into said progenitor cells.

BMP4 is described in more detail above. The humanised CDM may comprise from 1 to 100 ng/ml of BMP4, preferably about 10 ng/ml.

The methods described herein produce populations of progenitor cells of a clinical grade which are fully compatible with clinical applications. Because they have a defined provenance, the populations are free of impurities; in particular cells, proteins or other molecules derived from non-human animals which may produce immune or other deleterious side effects in vivo.

Other aspects of the invention provides a population of progenitor cells produced by a method described herein and a population of progenitor cells produced by a method described herein for use in a method of treatment of the human or animal body, for example in the treatment of damaged or dysfunctional tissue. A population of ectoderm progenitors may be useful, for example, in the treatment of damaged or dysfunctional nervous tissue, a population of mesoderm progenitors may be useful in the treatment of damaged or dysfunctional muscle, heart, kidney, vascular or haematopoietic tissue and a population of endoderm progenitors may be useful in the treatment of damaged or dysfunctional pancreas, liver, lungs, gut, and thyroid tissue.

Other aspects of the invention provide the use of a population of ectoderm progenitor cells produced by a method described herein in the manufacture of a medicament for use in the treatment of damaged or dysfunctional nervous tissue; the use of a population of mesoderm progenitor cells produced by a method described herein in the manufacture of a medicament for use in the treatment of damaged or dysfunctional muscle, heart, kidney, vascular or haematopoietic tissue; and the use of a population of endoderm progenitor cells produced by a method described herein in the manufacture of a medicament for use in the treatment of damaged or dysfunctional pancreas, liver, lungs, gut, or thyroid tissue.

Preferably, progenitor cells produced as described herein are clinical grade progenitor cells for therapeutic applications.

Aspects of the invention also extend a pharmaceutical composition, medicament, drug or other composition comprising a progenitor cell or population of progenitor cells, a method comprising administration of such a progenitor cell or population thereof or composition to a patient, e.g. for treatment (which may include preventative treatment) of damaged or dysfunctional tissue, as described above, and a method of making a pharmaceutical composition comprising admixing such a progenitor cell or population with a pharmaceutically acceptable excipient, vehicle or carrier, and optionally one or more other ingredients.

A progenitor cell or progenitor cell population which is administered to an individual may be genetically manipulated to produce a therapeutic molecule, for example a drug or growth factor (Behrstock S et al, Gene Ther 2006 March; 13(5):379-88, Klein S M et al, Hum Gene Ther 2005 April; 16(4):509-21)

The present invention provides a composition containing a progenitor cell or population produced in accordance with the invention, and one or more additional components. Pharmaceutical compositions according to the present invention, and for use in accordance with the present invention, may comprise, in addition to the progenitor cell(s), a pharmaceutically acceptable excipient, carrier, buffer, preservative, stabiliser, anti-oxidant or other material well known to those skilled in the art. Such materials should be non-toxic and should not interfere with the activity of the progenitor cell. The precise nature of the carrier or other material will depend on the route of administration.

Liquid pharmaceutical compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

Cells may be implanted into a patient by any technique known in the art (e.g. Lindvall, O. (1998) Mov. Disord. 13, Suppl. 1:83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-1555, Le Blanc et al, Lancet 2004 May 1; 363 (9419):1439-41).

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

A population of progenitor cells produced by a method described herein may also be useful in screening methods.

A method of screening for a compound useful in the treatment of damaged or dysfunctional tissue may comprise;
 contacting a population of progenitor cells produced by a method described above with a test compound and.
 determining the growth or differentiation of the progenitor cells.

An increase in the growth or differentiation of the progenitor cells in the presence of the test compound, relative to controls, is indicative that the test compound is useful in the treatment of damaged or dysfunctional tissue. A population of ectoderm progenitors may be useful, for example, in screening for compounds useful in the treatment of damaged or dysfunctional nervous tissue. An increase in the differentiation of the progenitor cells into neural cells may be indicative that the test compound is useful in the treatment of damaged or dysfunctional nervous tissue. A population of mesoderm progenitors may be useful in screening for compounds useful in the treatment of damaged or dysfunctional muscle, heart, kidney, vascular or haematopoietic tissue. An increase in the differentiation of the progenitor cells into cells of a specific tissue, such as muscle, heart, kidney, vascular or haematopoietic cells, may be indicative that the test compound is useful in the treatment of damaged or dysfunctional tissue of that type. A population of endoderm progenitors may be useful in screening for compounds useful in the treatment of damaged or dysfunctional pancreas, liver, lungs, gut, and thyroid tissue. An increase in the differentiation of the progenitor cells into cells of a specific tissue, such as pancreas, liver, lungs, gut, or thyroid cells, may be indicative that the test compound is useful in the treatment of damaged or dysfunctional tissue of that type.

The growth and/or differentiation of a progenitor cell may be determined using routine techniques.

Another aspect of the invention provides a method of expanding a population of human pluripotent cells comprising;
 culturing one or more human pluripotent cells in a humanised chemically defined medium (CDM) supplemented with fibroblast growth factor 2(FGF2) and Activin (CDM/AF);
 thereby expanding said population of human pluripotent cells.

Humanised chemically defined medium is described in more detail above.

Following expansion, the human pluripotent cells may be induced to differentiate, using a method described herein.

In some embodiments, a human pluripotent cell for use in any of the methods described above may be genetically manipulated, for example to reduce or silence expression of one or more genes or to express a heterologous polypeptide. In other embodiments, progenitor cells produced by any of the methods described above may be genetically manipulated following differentiation as described herein.

Progenitor cells or human pluripotent cells as described herein may be genetically manipulated, for example by the introduction of a heterologous nucleic acid, such as a nucleic acid construct or vector, into the cells in the culture medium. This may be useful in expressing a marker or reporter gene or a therapeutic or other sequence of interest or in expressing a suppressor such as an RNAi molecule to suppress or silence expression of one or more target genes.

When introducing or incorporating a heterologous nucleic acid into a cell, certain considerations must be taken into account, well known to those skilled in the art. The nucleic acid to be inserted should be assembled within a construct or vector which contains effective regulatory elements which will drive transcription in the target cell. Suitable techniques for transporting the constructor vector into the cell are well known in the art and include calcium phosphate transfection, lipofectin, DEAE-Dextran, electroporation, liposome-mediated transfection, lipofecamine-mediated transfection, and transduction using retrovirus or other virus, e.g. vaccinia or lentivirus (Vallier et al. 2004). For example, solid-phase transduction may be performed without selection by culture on retronectin-coated, retroviral vector-preloaded tissue culture plates.

Many known techniques and protocols for manipulation and transformation of nucleic acid, for example in preparation of nucleic acid constructs, introduction of DNA into cells and gene expression, and analysis of proteins, are described in detail in *Protocols in Molecular Biology*, Second Edition, Ausubel et al. eds. John Wiley & Sons, 1992 and *Molecular Cloning: a Laboratory Manual:* 3rd edition, Sambrook & Russell, 2001, Cold Spring Harbor Laboratory Press.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described above and tables described below.

Figure 7:
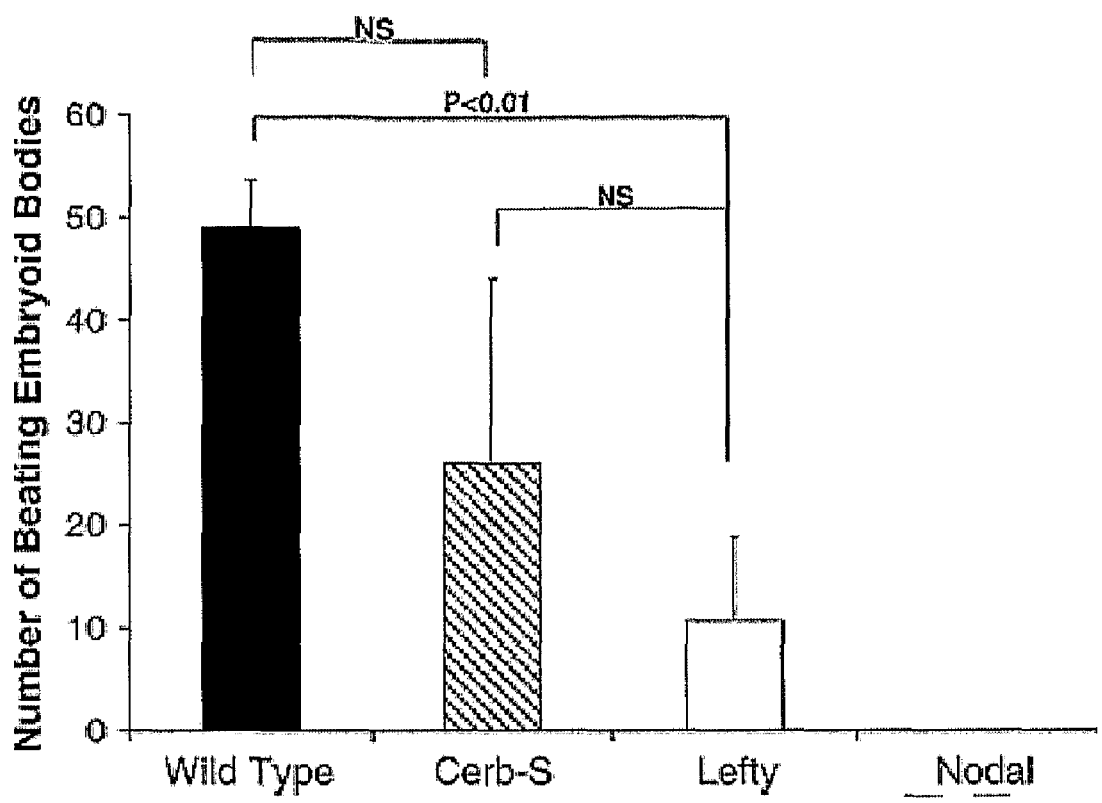

FIG. 7 shows the incidence of beating structures in Lefty expressing EBs. Lefty, Cerb-S expressing and wildtype EBs were plated in MEF media, and beating EBs were counted. Lefty expressing EBs generated fewer beating structures as compared to wildtype EBs (NS=not significant) (Scale bar=200 µM).

Figure 8:
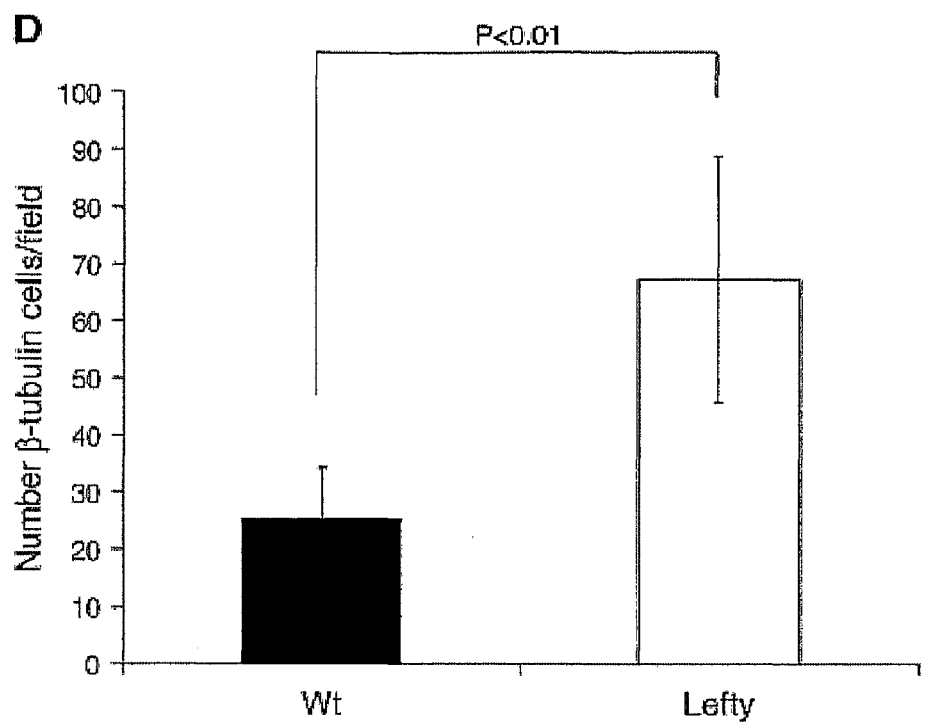

FIG. 8 shows quantitation of β-tubulin III positive cells in 6 independent experiments from Lefty expressing and wildtype cells grown as a monolayer revealed a Lefty induced increase in the number of β-tubulin III positive cells.

Figure 9:
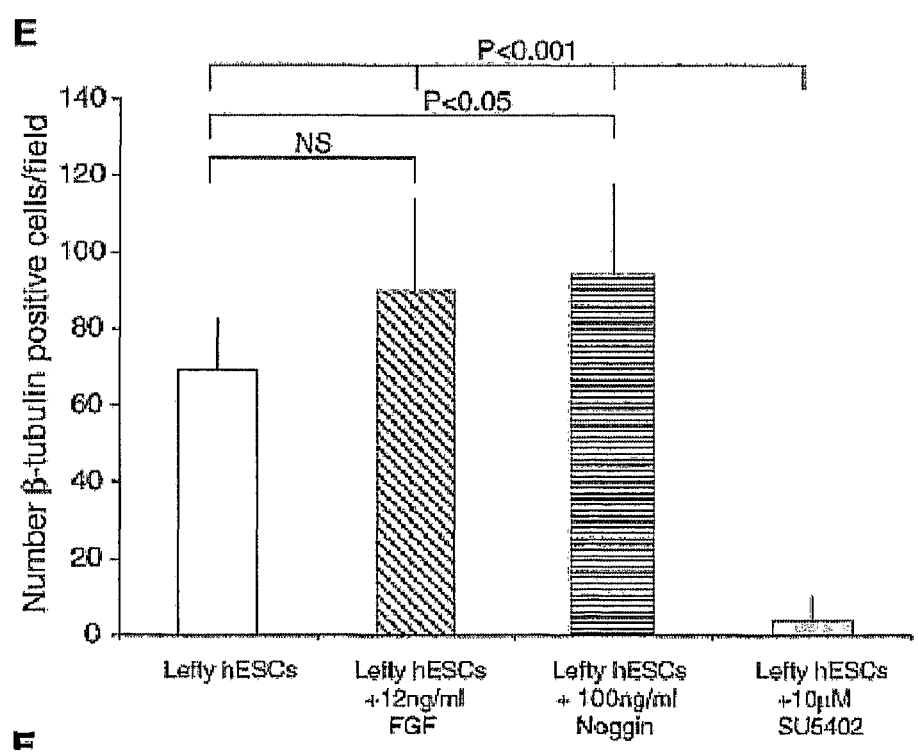

FIG. 9 shows quantitation of β-tubulin III positive cells in 6 independent experiments from Lefty expressing cells grown in feeder free conditions as a monolayer and then differentiated in CDM media containing either FGF (12 ng/ml), the BMP inhibitor Noggin (200/ml) or FGF receptor inhibitor SU5402 (20 µM). Lefty expressing hESCs exposed to FGF did not show a significant increase in the number of β-tubulin III positive cells as compared to controls, whereas Noggin produced a significant increase in β-tubulin III positive cells. Interestingly, inhibition of FGF signalling by SU5402 resulted in a significant reduction in neuron formation as shown by β-tubulin III immunoreactivity.

Figure 10:
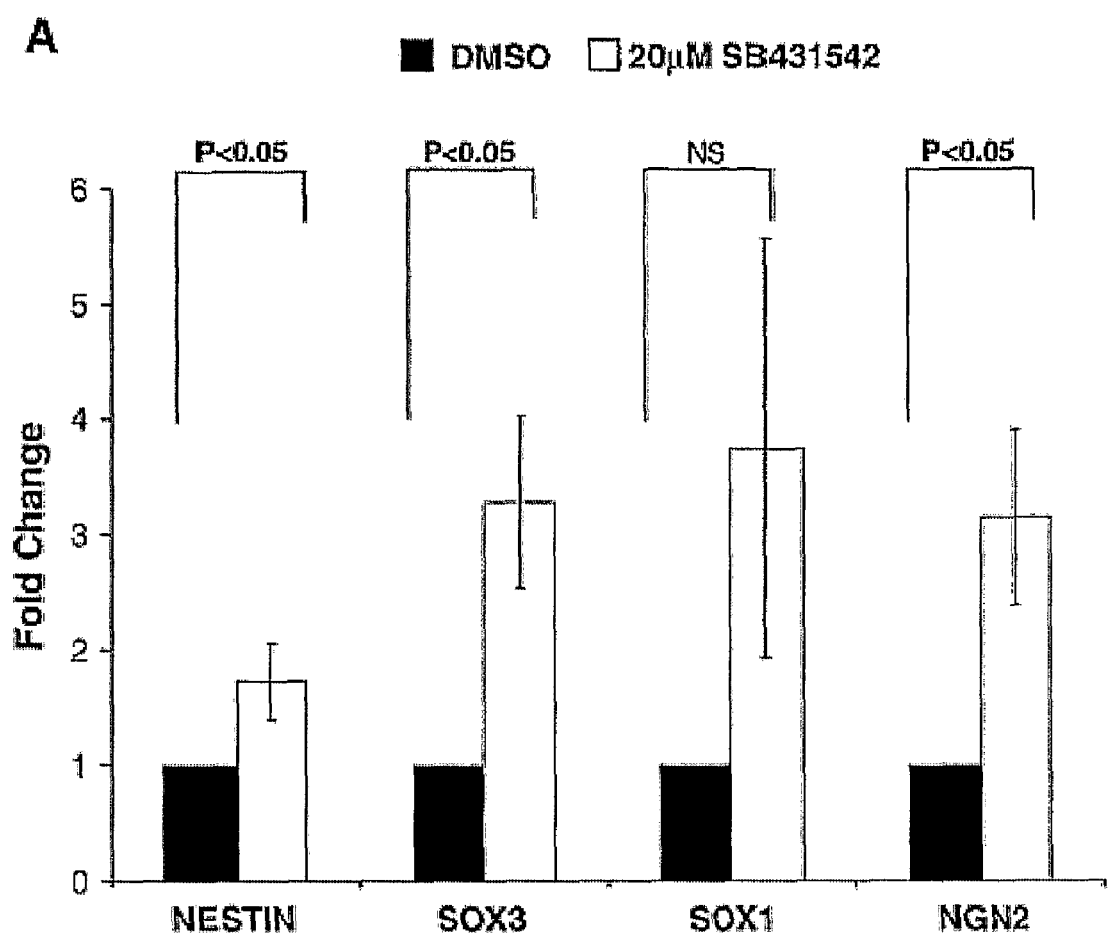

FIG. 10 shows real time qPCR analysis on DMSO- and SB431542 (20 µM)-treated EBs cultured for 14-16 days. Activin/Nodal inhibition led to an average increase in Nestin, Sox3, and NGN2 expression. Five independent batches of DMSO- and SB431542-treated EBs were used for this analysis.

Table 1 shows the expression of pluripotent markers in H9 and hSF-6 hESCs grown in CDM and hu-CDMs over a prolonged period of time. H9 or hSF-6 cells were grown for the indicated number of passages in feeders free and serum free conditions on human Fibronectin, Foetal Bovine Serum pre-coated plates (FBSc) or human Serum pre-coated plates (HSc). FACs was used to determine the fraction of cells expressing Tra-1-60 or SSEA-3. H9 grown on feeders in medium containing Serum Replacer (SR) were used a positive control. Similar values were obtained in three separate experiments.

Table 2 and Table 3 show the screening of culture conditions for inducing mesoendoderm differentiation into CDM. H9 hESCs were grown for 7 days or more in CDM-BSA or CDM-PVA supplemented with different growth factors (Activin, BMP4, FGF2) or inhibitors (SU5402 for FGF, SB431542 for Activin/Nodal/TGFβ, BIO for βCatenin). Then, immunostaining analysis were used to determine the fractions of cells expressing the pluripotent marker Oct-4, neuroectoderm marker Sox2, the mesoderm marker Brachyury, and the endoderm marker Sox17. The quantities of expressing cells were divided into five arbitrary categories. 0 for absence of expression, VL for expressing cells <1%, L for expressing cells <5%, H for expressing cells >10%, VH for expressing cells >50%. IN red are indicated the conditions allowing the generation of mesendoderm cells expressing Brachyury or Sox17.

Table 4 shows microarray analysis of hESCs grown for 36 h in CMD alone or CDM plus 10 ng/ml BMP4. The change in RNA expression of genes associated with particular cell types is indicated in the following panels. Table 4a lists genes down-regulated in the presence of BMP4. Table 4b lists genes up-regulated in the presence of BMP4. In all tables, the 'margin' value represents the fold change in mRNA expression (log 2 scale) with a negative value indicating down regulation after BMP4 treatment compared to CDM alone. The p-value and q-value are indicative of statistical significance, with a value less than 0.05 deemed significantly different between treatments.

EXPERIMENTS

Materials and Methods hESCs Culture in Feeder Free and Serum Free Conditions

H9, H1 (WiCell Inc., Madison, Wis., USA) and hSF6 (UCSF, San Francisco Calif., USA) hESCs were routinely cultured as described (Schatten et al., 2005) in KSR medium containing KO-DMEM supplemented with Serum Replacement (Invitrogen), glutamate (1 mM) and β mercaptoethanol (0.1 mM).

For feeder and Serum free culture, H9 and H1 and hSF-6 hESCs grown on feeders were harvested using 5 mg/ml collagenase IV (Gibco) and then plated into plates (Costar) pre-coated with 15 µg/ml of human fibronectin (Chemicon) for 20 minutes at 37 C and then washed twice in PBS. Alternatively, hESCs were plated into plates (Costar) pre-coated with human serum Foetal Bovine Serum for 24 hours at 37 C and then washed twice in PBS to eliminate any serum. Alternatively, cells were harvested using 1 mg/ml collagenase IV (Gibco) and then plated into 60 mm plates (Costar) pre-coated with 0.1% porcine gelatine (Sigma) and containing irradiated mouse embryonic fibroblasts.

hESCs were then grown in chemically defined medium (CDM), (Johansson and Wiles, 1995) supplemented with Activin (10 ng/ml, RandD systems) and FGF2 (12 ng/ml, RandD systems). The composition of CDM was 50% IMDM (Gibco) plus 50% F12 NUT-MIX (Gibco), supplemented with 7 µg/ml of insulin (Roche), 15 µg/ml of transferrin (Roche), 450 µM of monothioglycerol (Sigma) and 0.5 mg/ml bovine serum albumin fraction V (Europabioproducts). For the humanised version of CDM, BSA was replaced by human Serum Albumin, Plasminate™, Buminate™, or polyvinyl alcohol (PVA). Every 4 days, cells were harvested using 5 mg/ml collagenase IV (Gibco) or Accutase™ (Innovative Cell Technologies Inc CA) then plated into plates pre-coated with fibronectin or serum.

Karyotype analyses were performed on H9 and hSF-6 cells at various passages. Abnormalities were not observed even at late passages (p120) providing indication that genetic stability of hESCs was improved in CDM.

Generation of Expression Constructs and Stable Transfection

Plasmid pTP6 (Pratt et al., 2000) containing the CAGG (hCMV/Chicken β-Actin chimeric promoter) driving the expression of GFP-IRES-Puromycin, was used as the basis for constructing Lefty and Cerb-S expression vectors. pTP6 was digested with EcoR1, removing the GFP open reading frame (ORF), and either mouse Lefty2 or *Xenopus* Cerb-S ORFs were cloned into this site to generate pTP6-Lefty2 and pTP6-Cerb-S respectively. For stable expression with vectors encoding Lefty2 or Cerb-S, 3 confluent 60 mm plates containing around 2000 hESC colonies each were plated onto one 6 well gelatin-coated plate containing mouse feeders. After 48 h the cells were transfected using Lipofectamine 2000 (Invitrogen) as described (Vallier et al., 2004b). Three days after transfection, the cells were passaged onto 60 mm gelatin-coated tissue-culture plates containing puromycin-resistant mouse feeders. After 3 additional days, puromycin (1 µg/ml final concentration) was added. Puromycin-resistant colonies that appeared by 12 days of selection were picked, dissociated and plated onto 24-well gelatin-coated, feeder containing plates and expanded for further analysis as described above.

Differentiation of hESCs in Chemically Defined Conditions.

hESCs grown in Feeder free and serum free conditions were harvested using 5 mg/ml collagenase IV then plated into plates pre-coated with fibronectin. hESCs were grown for 48 hours in CDM supplemented with Activin (10 ng/ml, RandD systems) and FGF2 (12 ng/ml, RandD systems). To induce extra-embryonic differentiation, hESCs were grown for 5 additional days in CDM supplemented with BMP4 (10 ng/ml, RandD systems). To obtain neuroectoderm progenitors, hESCs were grown in CDM or in CDM-PVA in the presence of SB431542 (10 µM Tocris) and FGF2 (12 ng/ml, RandD systems) for 7 additional days. The resulting cells were grown in non-adherent conditions for 10 days and then plated back for 5 additional days in CDM to obtain fully differentiated neuronal cells. To obtain mesendoderm precursors, hESCs were grown for 3 additional days in CDM-PVA in the presence of SU5402 (10 µM, Calbiochem) and Activin (5 ng/ml, RandD systems). On the fifth day after passaging, the resulting cells were grown in CDM-PVA in the presence of BMP4 (10 ng/ml, RandD systems), FGF2 (20 ng/ml, RandD systems) and Activin (30 ng/ml or 100 ng/ml, RandD systems).

Lefty or Cerb-S expressing hESCs (as well as wildtype H9 and hSF-6 hESCs) were grown in 6 cm dishes (Corning), on mouse feeders. When confluent, hESCs were passaged using collagenase 1 mg/ml, as previously described (Schatten et al., 2005) and cultured in non-adherent conditions in CDM supplemented with either SU5402 (Calbiochem; 10 µM), SB431542 (Tocris; 20 µM), FGF-2 (R&D Systems; 12 ng/ml) or Noggin 200 ng/ml.

In some experiments, hESCs were incubated in DMEM supplemented with 10% FCS and 1 mM glutamine (MEF media) to promote mesoderm formation. EBs were then grown for 12-16 days at 37° C. at 5 CO2 before being harvested for histological or molecular marker analysis.

In some experiments, EBs grown in CDM were plated directly on fibronectin, and plated cells were either cultured in CDM alone or supplemented with either FGF-2 (R&D Systems; 12 ng/ml), Noggin (R&D systems; 200 ng/ml), or SU5402 (Calbiochem; 10 µM).

In some experiments, Wildtype and Lefty expressing hESCs were grown on fibronectin in FGF (12 ng/ml)/Activin (20 ng/ml) as a monolayer in the absence of a feeder layer (Vallier et al., 2005). When cells were 70-80% confluent medium was changed to either CDM only, CDM/FGF (12 ng/ml), CDM/Noggin 200 ng/ml, CDM/SU5402 and differentiated for 24 days.

Differentiation of Neuroectoderm Progenitors

Differentiation of neuroectoderm progenitors was induced by embryoid body (EB) formation. This was accomplished by incubating colonies treated with SB431542 for 7 days in medium containing 1 mg/ml collagenase IV without FGF for 6 hours, after which all the colonies had detached from the plate. The colonies were then rinsed once in the corresponding medium to be used for differentiation and grown in non-adherent conditions to generate EBs. The medium used for differentiation was the CDM.

To obtain neuronal outgrowths from EBs in adherent conditions, they were plated in 6 well plates after 15 days of differentiation as EBs. To allow EB adhesion in CDM, plates were pre-coated with fibronectin for 24 hours at 37 C and then washed twice in PBS. Plated EBs were then grown for 10 additional days in CDM.

Flow Cytometry and Cell Sorting

For detection of Tra-1-60, SSEA-3, N-CAM, CXCR4 and PDGFαRecptor adherent cells were washed twice in PBS then incubated for 20 minutes at 37 C in cell dissociation buffer (Invitrogen). Cells were then dissociated by gentle pipetting and resuspended at approximately 0.1 to 1.0×105 cells/ml in PBS+3% normal goat serum containing 0.1% azide (NGS) (Serotec). Cells were incubated for 20 minutes at 4 C with Tra-1-60 (1:100, Santa-Cruz), SSEA-3 (1:100, Santa-Cruz), CXCR4 (1:50, Pharmingen), N-CAM (1:200, Pharmingen), and PDGFαR (1:50, Pharmingen) or the corresponding isotype control (mouse IgM isotype control, Sigma; rat IgM isotype control, Sigma; mouse IgG isotype control, Pharmingen;). Cells were then washed twice in PBS+3% NGS and incubated when necessary for 20 minutes on ice with FITC-conjugated goat anti-mouse IgM antibody, (1:200, Sigma); FITC-conjugated goat anti-rat IgM antibody (1:300, Jakson laboratory) and FITC-conjugated goat anti-mouse IgG antibody (1:200, Sigma). Subsequently, cells were resuspended in PBS+3% NGS for stained with 7-aminoactinomycin D (7-AAD) viability dye (Immunotech) at 20 µL/mL for 15 minutes at room temperature. Live cells identified by 7-AAD exclusion were analyzed for surface-marker expression using FACSCalibur.

RNA Extraction and Real Time PCR

Total RNAs were extracted from hESCs or differentiated progenitors using the RNeasy Mini or Micro Kits (Qiagen). Each sample was treated with RNAse-Free DNAse (Qiagen) in order to avoid DNA contamination. For each sample 0.6 µg of total RNA was reverse transcribed using Superscript II Reverse Transcriptase (Invitrogen). Real time PCR reactions mixture were prepared as described (SensiMiX protocol Quantace) then were denatured at 94° C. for 5 minutes and cycled at 94° C. for 30 seconds, 60° C. for 30 seconds, and 72° C. for 30 seconds followed by final extension at 72° C. for 10 minutes after completion of 40 cycles. Primer sequences were described elsewhere (Vallier et al, 2003; d'Amour et al, 2005). All the PCR reactions were performed using a Stratagene Mx3005P in duplicate and normalised to PBGD in the same run.

For some RT-PCR experiments, 50-100 ng of RNA were used for each RT-PCR reaction, using the OneStep RT-PCR kit according to manufacturer instructions. For real-time PCR, 1 µg RNA was reverse-transcribed using the Qiagen QuantiTect Reverse Transcription kit. 1/20-1/40 of each cDNA reaction was used for each real-time PCR reaction using the QuantiTect SYBR Green PCR Kit (Qiagen) according to manufacturer instructions. Relative quantification of gene expression was done by normalising the detected levels of gene of interest mRNA to those of the house-keeping GAPDH gene. All primers were purchased from Qiagen, with the exception of Xenopus Cerb-S: Forward 5'-CTGTGACAGGATGGTGATAC-3' (SEQ ID NO: 1); Reverse 5'-ATGGTGCAGGGTAG TAGATG-3' (SEQ ID NO: 2). Mouse Lefty2: Forward 5'-GGAGATGTACCTGGACCTGC-3' (SEQ ID NO: 3); Reverse 5'-CATCTGAGGCGCAGCTA-CAG-3' (SEQ ID NO: 4).

Microarray Methods

Sample RNA was hybridized to Affymetrix hg-u133+2 GeneChips ©. All sample arrays were background corrected, normalized and summarized using default parameters of the RMA model. Array processing was performed using the affy package of the Bioconductor (found on the world wide web at the hypertext protocol transfer address of "bioconductor.org") suite of software for the R statistical programming language (found on the world wide web at the hypertext protocol transfer address of "r-project.org"). The resulting data set contained processed gene expression values for 54675 probe-sets. Analysis of Differential Regulation: The moderated t-statistic of 5, implemented in the Limma package of Bioconductor, was employed to assess the significance of differential gene (probe-set) expression between sample groups. In order to reduce errors associated with multiple hypothesis testing on such a scale, the significance p-values obtained were converted to corrected q-values using the FDR method.

Probe-sets with associated $q<0.01$ (FDR 1%) were deemed to exhibit significant differential expression between sample groups. Data Visualisation: Heat maps of gene expression were created by importing relevant subsets of RMA processed microarray gene expression data into the dChip v1.3 microarray analysis package (found on the world wide web at the hypertext protocol transfer address of "biostat.harvard.edu/complab/dchip/"). In the case wherein a gene is represented by more than one probe-set on the array, a single probe-set was chosen to represent gene expression in the heat map according to highest mean expression over all samples (i.e. the most reliable sample hybridization regardless of group membership).

Immunofluorescence

HESCs or differentiated progenitors were fixed for 20 minutes at 4° C. in 4% paraformaldehyde (PFA) and then washed three times in PBS. Cells were incubated for 20 minutes at room temperature in PBS containing 10% goat serum (Serotec) and subsequently incubated over night at 4° C. with primary antibody diluted in 1% goat serum in PBS as follows: SSEA-3 (1:100, Santa Cruz), SSAE-1 (1:25), Tra-1-60 (1:100, Santa CruZ), Oct-4 (1:100, Abcam ab18976 or SantaCruz), Sox2 (1:100, Abcam ab15830), Alkaline Phophatase (1:50, Abcam ab17989), Brachyury (1:100, Abcam ab20680 or RandD systems), Sox17 (RandD systems), FoxA2 (1:50, Abcam ab5074), GATA4 (1:250, Santa CruZ), GATA6 (1:200, Abcam ab22600 or Santa Cruz), Vent-2 (1:100, Abcam ab20913), Goosecoid (1:25, Abcam ab21059), Wnt3A (1:100, Abcam ab19925), CXCR4 (1:100, RanD Systems or Pharmingen). Nestin (1:200, Abcam ab5968), NCAM (1:100, Abcam ab8077), GFAP (ZZ), Neurofilament (ZZ), βIII Tubulin (ZZ), Glutamate (ZZ), N-Cadherin (1:100, Abcam ab18203 or ZZ). Cells were then washed three times in PBS and incubated with fluorescein-Isothiocyanate-conjugated anti-mouse IgG or IgM (Sigma 1:200 in 1% goat serum in PBS) or rat IgM (Jackson laboratory 1:300 in goat serum in PBS) or rabbit IgG (Jackson laboratory 1:200 in donkey serum in PBS) for two hours at room temperature. Unbound secondary antibody was removed by 3 washes in PBS. Hoechst 33258 was added to the first wash (Sigma 1:10000).

In Situ Hybridisation

EBs were fixed in 4% PFA in PBS at 4° C. o/n, and stored in methanol at −20° C. In situ hybridisation was performed as described previously (Harland, 1991), with slight modifications.

Southern Blot Analysis

Genomic DNA was isolated from hESCs using QIAGEN Genomic-Tip 100/G according to the manufacturers' instructions. 10 mg of genomic DNA was digested with Xba1 (60 units) for 16 h Southern blot and hybridisation and using [P32] dCTP labelled probe has been described previously (Sambrook et al., 2001). Probe used corresponds to the first 600 bp of the CAG promoter.

Humanised Chemically Defined Medium to Grow hESCs.

Figure 1:
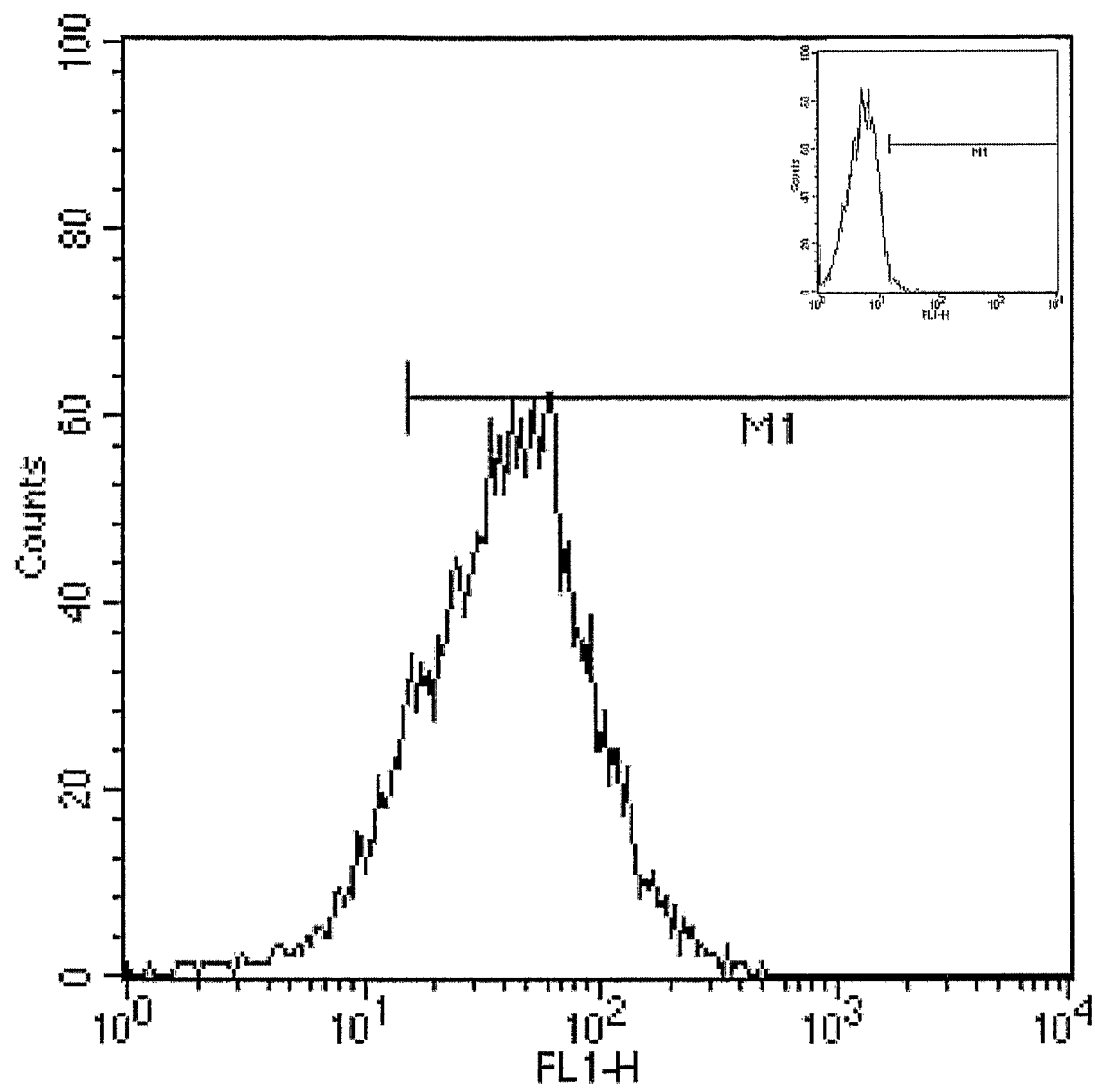
FIG. 1 shows the fraction of cells expressing the pan neuronal marker N-CAM in hESCs before and after inhibition of Activin signalling using SB431542 in presence of FGF2. Fraction of cells expressing N-CAM was determined using FACs after 7 days treatment.
Figure 2:
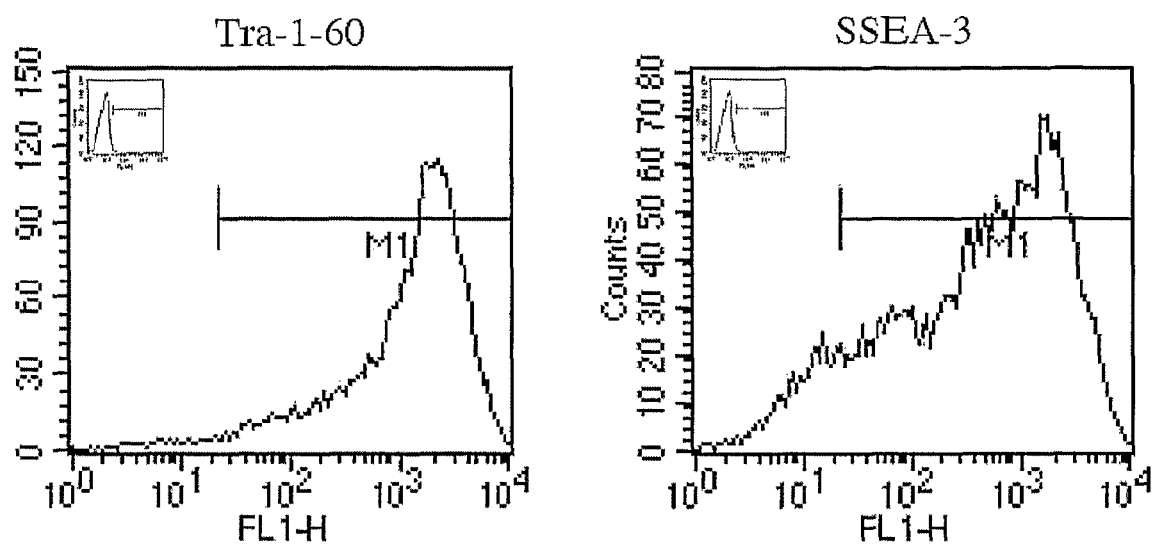
FIG. 2 shows the fraction of cells expressing Tra-1-60 and SSEA-3 in hESCs grown over prolonged periods in CDM/AF on fibronectin coated plates. Fraction of cells was determined using FACs.

We, and others, have recently shown that Activin and FGF are capable of maintaining the pluripotent status of hESCs. Based on these results, we developed chemically defined culture conditions to grow hESCs in absence of serum and feeders. This approach is a based on a chemically defined medium (CDM) containing only insulin, transferin, defined lipids, Bovine Serum Albumin (BSA), Activin 10 ng/ml, FGF2 12 ng/ml. hESCs can be grown on FBS coated plates in CDM+Activin+FGF (CDM/AF) over prolonged period of time during which they remain pluripotent and maintain a normal karyotype (Vallier et al., 2005). To obtain fully defined culture conditions, we replaced FBS coating of the plates by extra-cellular matrix (ECM) proteins of human origins including human serum, fibronectin, Laminin, vitronectin, Poly-L-Lysin or collagen IV. Efficient adhesion of hESCs was only observed with Fibronectin and human serum while only differentiated cells seems to attach properly on other ECM. H1, H9 and hSF-6 hESC lines were grown over prolonged periods in CDM/AF on fibronectin coated plates while continuing to express the pluripotent markers Oct4, Sox2, Alkaline Phosphatase, SSEA-3 and Tra-1-60. FACs analyses showed that the fraction of hESCs expressing the cell surface antigens Tra-1-60 and SSEA-3 could reach respectively 95% and 87% after 85 passages in these culture conditions (Table 1, FIG. 2). In addition, hESCs were capable to form teratomas when transplanted in immunodeficient mice confirming the pluripotent status of the cells grown in CDM/AF on fibronectin. Karyoptypic analyses were performed every 15 passages to insure that hESCs did not acquire genetic abnormalities. Methylation and bi allelic expression of imprinted genes remained normal in these culture conditions suggesting that they did not alter the epigenetic status of hESCs. Finally, stable transfection (Vallier et al, 2004) of an expression vector for the green fluorescent protein were performed successfully using lipofecamine 2000, leading to the generation of green fluorescent hESCs sub-lines. Together, these results provide indication that hESCs can be grown in fully defined condition in CDM/AF on Fibronectin coated plates without losing their pluripotency.

However, presence of animal products in the CDM/AF remains a limitation for clinical applications of this approach. Therefore, we decided to substitute BSA by equivalent products of human origin already used in clinics including Plasmanate™ (CDM-Plas), Buminate™ (CDM-Bum), human Serum albumin (CDM-hSA) or the artificial polymer Polyvinyl Alcohol (CDM-PVA). Results obtained with these humanised CDM (hu-CDM) were similar to those described above with CDM containing BSA (Table 1) with the exception of CDM-PVA in which hSF-6 cells differentiated after two passages. Adhesion of Fibronectin also appeared less efficient in CDM-Plas and CDM-Bum, and human serum coated plated were preferentially used with these media. Finally, to avoid the use of collagenase IV, hESCs grown in hu-CDM were passaged using Accutase, a dissociation buffer which contains neither bacterial nor mammalian derived products. H9 and hSF-6 cells were grown more than 20 passages while they maintain their pluripotent status and a normal karyotype using these culture conditions (Table 1). Taken together these results demonstrate that humanised CDMs can be used to grow hESCs over prolonged period in conditions compatible with clinical applications.

Screening of Culture Conditions for Driving Differentiation of hESCs Toward the Primary Germ Layers.

We then developed a method for inducing differentiation of hESCs into the three primary germ layers. Culture conditions inductive for mesoderm, endoderm and neuroectoderm were screened using an approach based on immunostaining analyses for the expression of proteins specifically expressed by pluripotent cells (Oct-4), neuroectoderm progenitors (Sox2 in absence of Oct4), endoderm progenitors (Sox17) and mesoderm progenitors (Brachyury). In summary, hESCs grown in CDM (CDM-BSA or hu-CDM) were plated on fibronectin in CDM-BSA/AF or CDM-PVA/AF. Then cocktails of growth factors (BMP4, FGF2, Activin) or chemical inhibitors (SU5402, SB431542) were added at different times and for different periods. After 7 to 10 days treatment, cells were fixed and then the expression of Oct-4/Sox2, Sox17 and Brachyury was analysed using immunostaining. The effect of three growth factors on the differentiation of hESCs into the primary germ layers was systematically analysed in our screen. We also studied the function of FGF and Activin signalling pathways in the maintenance of the pluripotent state by analysing the effect of the SU5402, a chemical inhibitor of FGF receptors, and the SB431542, a chemical inhibitor of Activin/TGFβ receptors. The conditions screened and the results obtained are summarised in tables 2 and 3.

BMP4 Induces Differentiation of hESCs into Extra-Embryonic Tissues.

In all the conditions tested in our screen, the addition of BMP4 (10 ng/ml) was capable to induce differentiation of hESCs into a homogenous population of cells with a cobblestone like morphology. These cells expressed neither the pluripotency markers Oct-4 and SSEA-3 nor the mesendoderm markers Sox17 and Brachyury. On the other hand, they expressed GATA6 and GATA4, two genes known to be involved in the specification of extra-embryonic tissues during early development. Real time PCR confirmed that the addition of BMP4 in CDM induced a significant decrease in the level of Oct-4 transcripts after only 16 hours (FIG. 2B) while in the mean time it strongly enhanced the expression of extra-embryonic markers including GATA6 and H19 (FIG. 2B). In addition, cells generated in these conditions expressed the transcripts coding for the genes SSEA-1, GATA4, GATA6, Sox7, CoupTFI, CoupTFII, and Sparc which are known to be expressed in the primitive endoderm layer at the blastocyst stage. On the other hand, expression of specific markers for trophectoderm were also observed, including CDX2, Hand1, H19, haCG and Eomes. Microarray analyses confirmed these results by showing a general increase in the level of expression of genes known to be expressed in extra-embryonic tissues during early development (Table 4). These results provide indication that the activation of BMP signalling is a very efficient inducer of differentiation in CDM and that it is sufficient to drive differentiation of hESCs toward extra-embryonic lineages. However, BMP4 in CDM did not appear to generate a homogenous population of trophectoderm cells as described by Xu and colleagues but rather a mixture of cells containing trophectoderm cells and primitive endoderm cells. The presence of unknown factors in the Matrigel and serum used in previous studies could explain this difference. All together these results demonstrated that CDM supplemented with BMP4 represents a unique in vitro system to generate extra-embryonic tissues in defined culture conditions which will be very advantageous for studying the molecular mechanisms involved in their specification.

Inhibition of Activin/Nodal Signalling Pathway is Sufficient to Induce Differentiation of hESCs into Neuroectoderm Progenitors.

Figure 3:
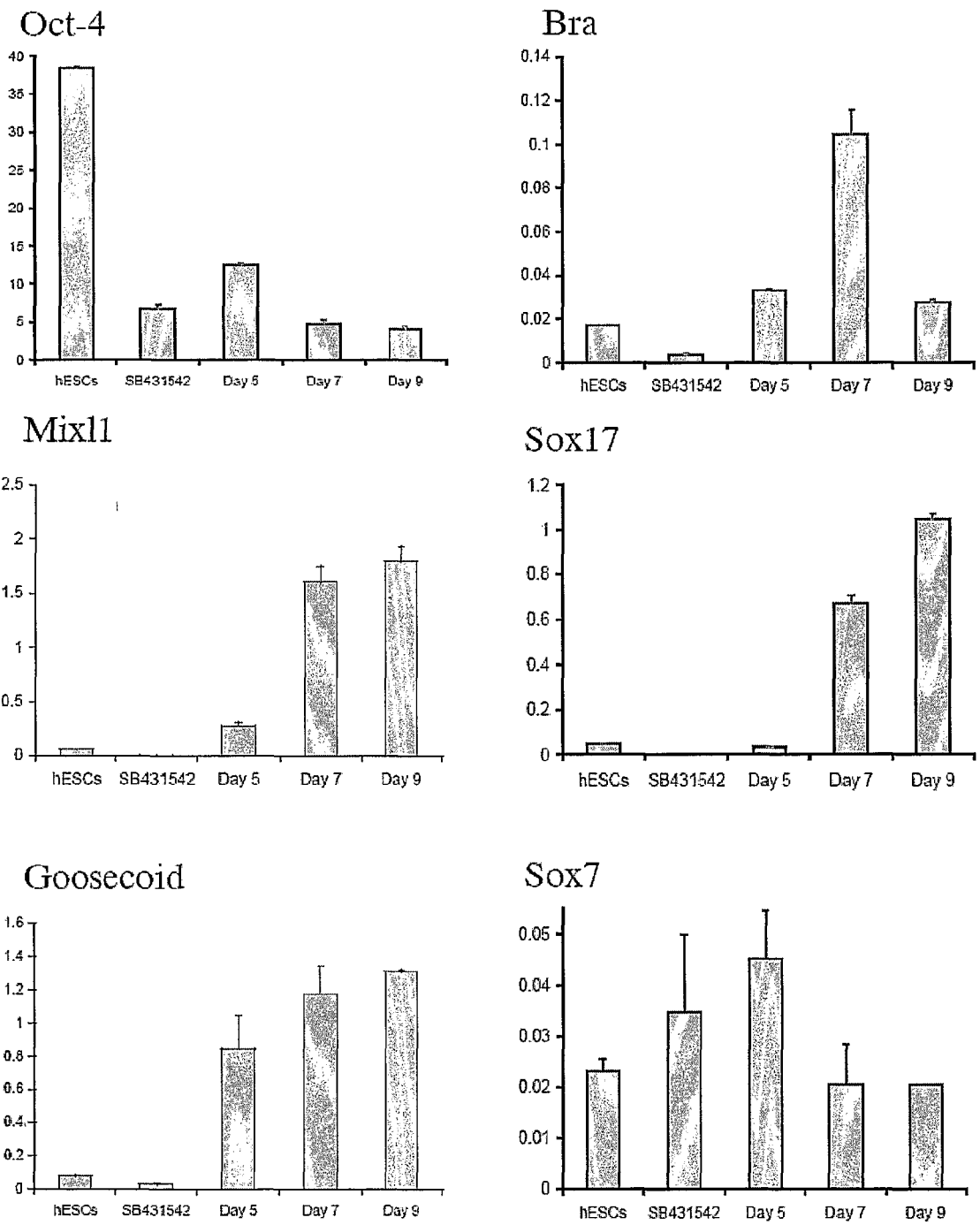
FIG. 3 shows the expression of different markers specific for the mesendoderm (endoderm/mesoderm) lineage in hESCs differentiated in CDM/PVA. Scale Bar 50 µM.

Another outcome from our screen was that inhibition of Activin signalling by the SB431542 systemically resulted in differentiation (Table 2 and 3). The addition of FGF2 or BIO, a GSK3β inhibitor, was not sufficient to rescue the expression of Oct4 providing indication that FGF and Wnt signalling were not sufficient to maintain the pluripotent status of hESCs. In addition cells expressing the mesendoderm markers Bra, Sox17, FoxA2, and αFP were never observed in the presence of SB431542 (FIG. 3, Table 2 and 3) confirming the importance of Activin signalling in the commitment of pluripotent stem cells toward this lineage. On the other hand, the addition of SB431542 in the presence of FGF2 resulted in the generation of highly proliferative cells which expressed Sox2 but not Oct4, SSEA-3, Tra-1-60 or Nanog. These cells also expressed the pan neuronal markers NCAM and Nestin. FACs analyses revealed that 80% of the cells grown for 7 days in the presence of FGF2 and SB431542 express NCAM against 4% in CDM/AF. Finally, Oct-4−/Sox2+ cells were further differentiated into population of neuronal cells expressing βIII-tubulin, Neurofilament, GFAP and Glutamate. Together these results revealed that a combination of SB431542 and FGF2 in CDM/PVA is sufficient to generate a homogenous population of neuroectoderm progenitors which possess the potential to differentiate into neuronal cells. Inhibition of BMP signalling was not required in our culture conditions since this pathway is not activated in hESCs grown in CDM (Vallier et al, 2005). Together these results demonstrate that inhibition of Activin signalling in CDM can be used to generate early neuroectoderm progenitors which represent a source of neuronal cells with clinical potential. This method of differentiation also represents a unique in vitro model to study the mechanisms controlling the specification of pluripotent cells toward the neuroectoderm lineage during early mammalian development.

Mesendoderm Differentiation of hESCs can be Induced in Chemically Defined Conditions Using BMP4, FGF and Activin.

Figure 4:
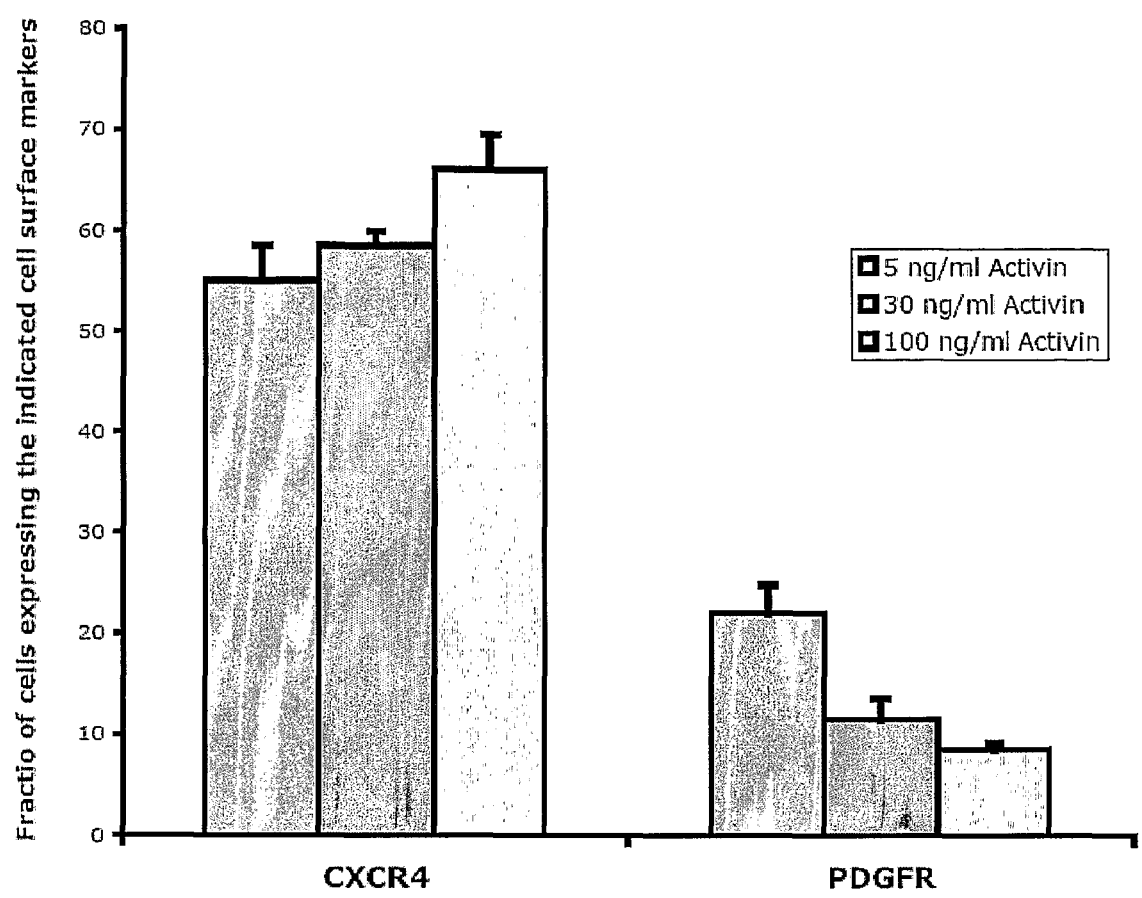
FIG. 4 shows the fraction of cells expressing the definitive endoderm marker CXCR4 and the mesoderm marker PDGFa after induction of differentiation in CDM PVA in presence of increasing dose of Activin. Fraction of cells expressing CXCR4 or PDGFa was determined using FACs after the third day in CDM+BMP+FGF+Activin.

Recent studies have clearly established that differentiation of human and mouse ESCs into mesendoderm cells in vitro is strictly dependent on Activin signalling. Our results partially reinforced these results since Sox17 or Bra expressing cells were never observed in the presence of SB431542 (Table 2 and 3). However, the addition of high doses of Activin in CDM-BSA or CDM-PVA was not sufficient to direct differentiation of hESCs into homogenous population of cells expressing mesendoderm markers. On the contrary, the addition of Activin systematically resulted in the maintenance of Oct-4 expression in a large fraction of the cell population (Table 2 and 3). To generate endoderm progenitors, previous studies have used medium containing Foetal bovine Serum, feeders and complex extracellular matrix. These undefined components represent a major difference with our culture system since they could provide unknown factors acting together with Activin to induce differentiation. Interestingly, we observed that inhibition of FGF signalling using the SU5402 increased the number of Bra and Sox17 expressing cells generated in presence of high dose of activin (Table 2 and 3) providing indication that FGF signalling reduced the efficiency of Activin signalling to induce mesendoderm differentiation. However, even in the absence of FGF signalling, most of the cells retained the expression of Oct4 while a small fraction of the cells express Sox17/Brachyury, indicating that other factors are involved in these mechanisms. Our screen of culture conditions confirmed this hypothesis since homogenous population of cells expressing Sox17 was only obtained with a three step protocols including combinations of different growth factors. In summary, hESCs grown in CDM or huCDM were plated for 48 hours on fibronectin in CDM PVA containing Activin and FGF2. This first step allowed the hESCs colonies to attach properly and as expected cells continued to express high level of Oct4, but not Brachyury or Sox17. Then, SU5402 (10 μM) and low dose of Activin (5 ng/ml) was added for the three following days. Addition of SU5402 reduced adhesion of the colonies which started to form compact aggregates of cells expressing Oct4 and low level of Bra but not Sox17. These observations suggest that this second step acts as pre-differentiation step where hESCs could not be specified toward neuroectoderm lineage because of the inhibition of FGF and the presence of Activin. The third step of the protocol consisted in adding a cocktail of BMP4 (10 ng/ml), FGF2 (20 ng/ml) and Activin (30 ng/ml or 100 ng/ml) which induced the spreading and the differentiation of the colonies. After 24 hours in these conditions, a majority of cells expressed high level of Bra while Oct4 expression declined. The following days, cell proliferation strongly increased and cells expressing Sox17 increased very quickly while the number of Bra or Oct4 expressing cells almost disappeared. Immunostaining analyses showed that these cells expressed markers of definitive endoderm including CXCR4, Goosecoid, FoxA2, GATA4, GATAG, Vent-2, WNT3, and N-Cadherin. In addition, transcripts of Sox7, a gene specifically expressed in extra-embryonic endoderm was not detected in this population of cells using RT-PCR. FACs analyses revealed that the proportion of cells expressing the definitive endoderm marker CXCR4 and the mesendoderm marker PDGFR depends on the dose of Activin added at the third step. In the presence of a high dose of Activin (100 ng/ml), 70% of the cells expressed CXCR4 while only 7% expressed PDGFR. On the other hand, in the absence of exogenous Activin, 55% of the cells remained positive for CXCR4 while 21% of the cells express PDGFR (FIG. 4). These results confirm that a high dose of Activin favours endoderm differentiation above mesoderm differentiation.

Equivalent results were obtained with two cell lines used in this study (H9 and hSF-6) demonstrating that this protocol is a robust approach for driving differentiation of hESCs toward the mesendoderm (i.e. mesoderm/endoderm) lineage.

Characterisation of Lefty and Cerb-S Expressing hESCs

Human ESCs grown in non-adherent conditions aggregate to form embryoid bodies (EBs) in which differentiation is initiated along both extra-embryonic and primary embryonic germ layer pathways (Vallier et al., 2004a). We used this model to study mechanisms controlling neuroectoderm specification of hESCs, as EBs reproduce three-dimensional cellular interactions. To explore the function of Nodal signalling in these EBs, we stably over-expressed Lefty2 and Cerb-S in the hESCs from which the EBs were derived, using the robust expression vector pTP6 (Pratt et al., 2000).

Southern blot analysis using the CMV promoter as a probe (first 600 bp of CMV/chicken β-Actin chimeric promoter) showed single copy integration for both Lefty and Cerb-S overexpressing hESC H9 lines. As expected, wildtype H9 genomic DNA did not hybridise with this probe. Only single copy integrants were used for further study. Stable clones generated using the Lefty-pTP6 vector (N=18 for H9 cell line and N=10 for hSF-6 cell line) and the Cerb-S-pTP6 vector (N=26 for H9 cell line and N=8 for hSF-6 cell line) were screened for Lefty or Cerb-S expression using RT-PCR. In addition, an hrGFP overexpressing hESC cell line (Vallier et al., 2004a) was included as a negative control in RT-PCR analysis along with wild type hESCs to control for any effects induced by the genetic manipulation procedure itself. The numbers of stably transfected colonies generated using the Lefty-pTP6 and Cerb-S-pTP6 vectors were similar to those generated using the hrGFP-pTP6 vector. Three independent clones for both Lefty and Cerb-S expressing H9 and hSF-6 hESCs were further characterised and used for subsequent experiments.

Lefty and Cerb-S Protein were Secreted from EBs of Either Lefty or Ceberus Expressing hESCs.

This was clear from the ability of supernatants of such cultures to induce differentiation of EBs derived from Nodal overexpressing hESCs. However, pluripotent Lefty and Cerb-S expressing hESC lines, like wildtype hESCs, expressed the pluripotency markers Oct4 and Tra-1-60 during a prolonged period of culture with feeder cells (30 passages/5 months). These results demonstrate that inhibition of the endogenously produced Nodal by either Lefty or Cerb-S expressing clones did not lead to differentiation of hESCs grown in conditions supportive of pluripotency. This could reflect the ability mouse feeders to secrete sufficient Activin to maintain pluri-potency under these conditions (Vallier et al., 2005). Furthermore, Lefty expressing hESCs grown in feeder-free conditions in CDM medium supplemented with Activin/FGF maintained their expression of pluripotent markers Oct4 and Tra-1-60 also indicating that Activin can circumvent the inhibiting effects of Lefty on Nodal Activity.

Lefty or Cerb-S Overexpression Drives Differentiation of hESCs Toward the Neuroectodermal Pathway at the Expense of Other Lineages.

Figure 5:
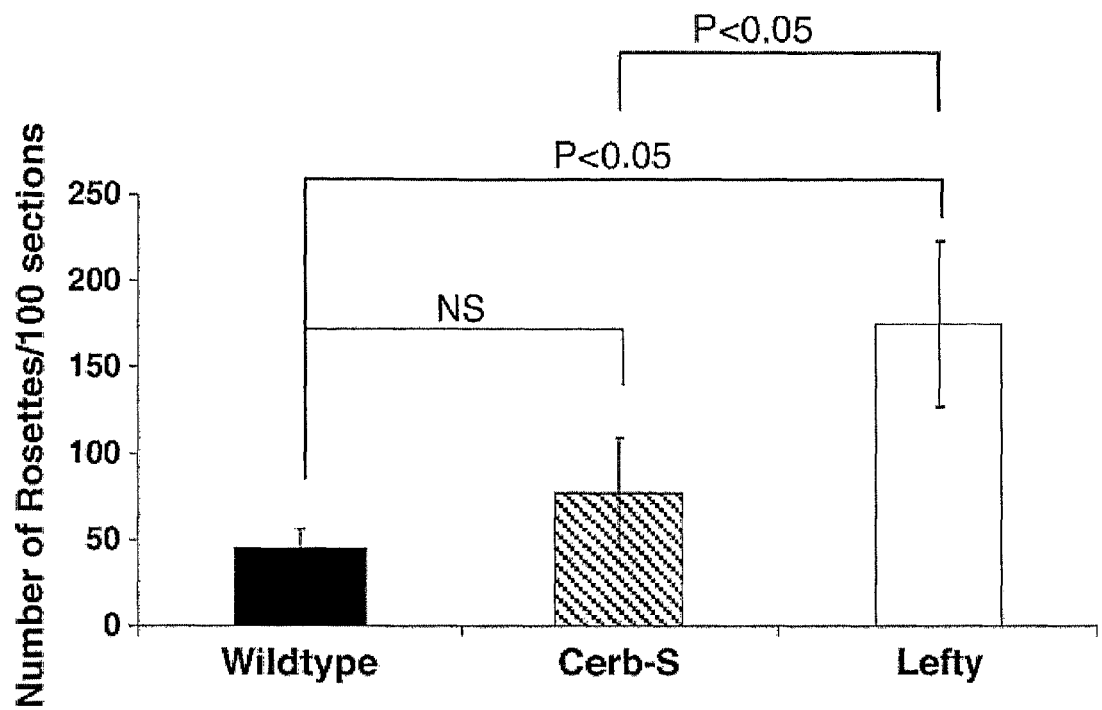
FIG. 5 shows quantitation of rosette structures in EBs of either Lefty or Cerb-S expressing and wildtype EBs. Lefty expressing EBs had significantly greater numbers of rosette structures as compared to Cerb-S and wildtype (NS=not significant) (Scale bar=200 µM).

To investigate the development of EBs derived from Lefty or Cerb-S overexpressing hESCs, we grew the cells as EBs in suspension culture using CDM medium. As previously observed (Vallier et al., 2004a), wildtype control EBs grown in CDM developed almost exclusively as simple spheres with no apparent tissue organisation. By contrast, the majority of EBs derived from Lefty overexpressing hESCs showed a unique phenotype, consisting of epithelial layers organised into regular folded structures and bearing a striking resemblance to the neural folds formed during early vertebrate development. Cerb-S expressing EBs showed an epithelial phenotype similar to Lefty EBs, but with fewer folded structures. Hematoxylin/Eosin staining of sectioned EBs confirmed that these folded structures found in Lefty overexpressing EBs were neuroectoderm-like, with internal epithelial rosettes. Lefty and Cerb-S expressing EBs contained respectively 5 times (Pb 0.05) and 2 times (not significant, N.S.) more epithelial rosettes than control EBs (FIG. 5). These results indicate that inhibition of the Activin/Nodal signalling pathway by Lefty produces a striking alteration of developmental fate of hESCs.

To test whether the EBs derived from either Lefty or Cerb-S overexpressing hESCs were neural in character, EBs were fixed, sectioned and immuno-stained for markers of definitive neuroectoderm (Nestin and Sox1), endoderm (Sox17) and mesoderm (Brachyury). Lefty and Cerb-S expressing EBs grown in CDM showed an overall increase in expression of the neuroectoderm markers Nestin and Sox1 compared to wildtype EBs, while there was a concomitant reduction in expression of the endoderm marker Sox17 in Lefty and Cerb-S expressing cells when EBs were grown in MEF medium, a condition known to promote mesendoderm specification.

Figure 6:
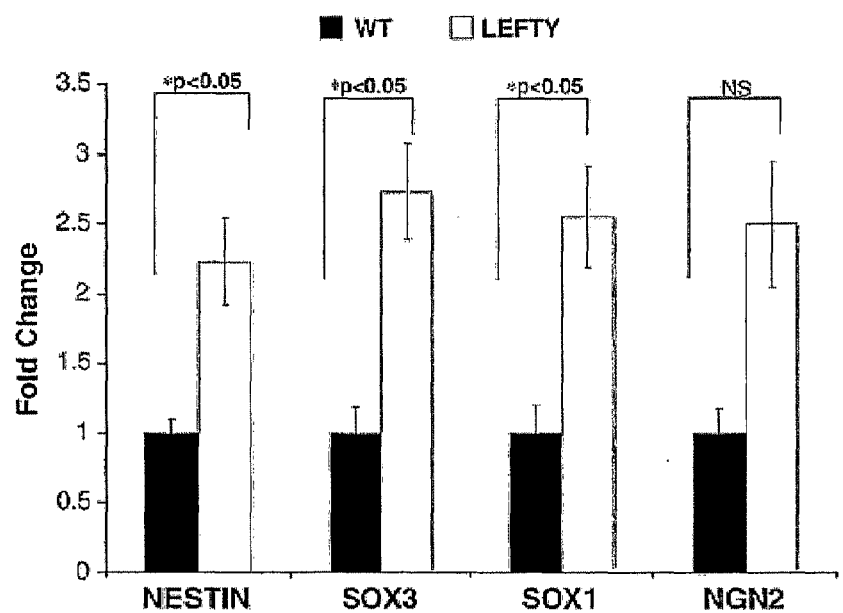
FIG. 6 shows Real-time qPCR analysis showed increased average levels of Nestin, Sox3 and Sox1 expression in Lefty expressing EBs as compared to wildtype. Four independent batches of WT and Lefty EBs were used for this analysis.

Brachyury expression was observed neither in control EBs nor in Lefty or Cerb-S expressing EBs. In situ hybridisation analysis supported these results, showing that at 14 days EBs derived from Lefty overexpressing hESCs showed up-regulation of the neuroectoderm markers Nestin and Sox3 and the neuronal differentiation marker Neurogenin2 (NGN2). In addition, Lefty expressing EBs showed a more pronounced down-regulation of the pluripotency marker Oct4 as compared to controls. Real time qPCR analysis was employed to quantify these effects. Comparison of the expression of Nestin, Sox3, Sox1 and NGN2 in four independent batches of WT and Lefty EBs showed a clear increase in the mean expression levels of most markers (Pb0.05 for Nestin, Sox3 and Sox1), though the levels of NGN2 was significantly greater (Student's T-test, P=0.094) (FIG. 6).

To evaluate further the differentiation potential of Lefty and Cerb-S overexpressing hESCs, EBs were cultured in MEF medium containing fetal bovine serum (FBS), which promotes the formation of mesoderm lineages including cardiomyocytes, as recognised by rhythmically beating structures. Lefty over-expressing EBs grown in these conditions displayed a decreased incidence of rhythmically contracting structures as compared to wildtype EBs, [~79% decrease for Lefty (P<0.01), ~53% for Cerb-S (NS)], providing indication of a reduced ability to generate mesoderm (FIG. 7). Nodal expressing EBs grown in these conditions were not seen to generate such beating structures, and instead maintained expression of the pluripotency marker Oct-4 (FIG. 7).

To observe the ability of Lefty and Cerb-S expressing EBs to differentiate into specific neuronal cell types, WT, Lefty or Cerb-S EBs grown for 12 days as suspension cultures in CDM were re-plated on FBS coated plates in CDM and cultured in these conditions for 12 more days. EBs derived from Lefty expressing hESCs (both H9 and hSF-6) showed a substantial neurite outgrowth as compared to Cerb-S and wildtype cells.

This was particularly evident when the cultures were stained with an antibody to the pan neuronal marker β-tubulin III. Cultures from plated Lefty and Cerb-S EBs were stained positive for the neurotransmitters Glutamate, GABA and for the astrocyte marker glial fibrillary acidic protein (GFAP), confirming that Activin/Nodal inhibition promotes specification of neural progenitors that are able, under appropriate conditions, to generate both differentiated neurons and astrocytes.

To quantify the neurogenic potential of Lefty expressing hESCs, we cultured Lefty expressing hESCs in feeder-free conditions as a monolayer in CDM supplemented with Activin and FGF as described previously (Vallier et al., 2005). When cells reached 70-80% confluency, medium was changed to CDM only, CDM plus FGF (12 ng/ml) (CDM/FGF), CDM plus the BMP inhibitor Noggin (200 ng/ml) (CDM/Noggin) or CDM plus the FGF receptor inhibitor SU5402 (10 μM) (CDM/SU5402), and cells were cultured in these conditions for 24 days Immunostaining for β-tubulin III, a neuronal marker revealed abundant neurons generated by Lefty expressing hESCs, although wildtype hESCs also showed a background level of neuronal differentiation in these conditions. The incidence of neural differentiation was determined by counting the number of β-tubulin III positive cells in random fields.

This showed that when differentiated in CDM, Lefty expressing hESCs generated more β-tubulin III positive cells/field (69±13) than wildtype cells (25±9) (P<0.01) (FIG. 8). FGF signalling was essential for neuronal differentiation in these conditions, as shown by the effect of the pharmacological inhibitor SU5402, which induced a significant loss of β-tubulin III positive cells (FIG. 9) (P<0.001). In addition, inhibition of BMP signalling significantly increased (P<0.05) the number of β-tubulin III positive cells, providing indication that BMPs may be released by differentiating cells in the cultures and restrain neural cell development. Interestingly, SU5402 treatment of differentiating Lefty expressing hESCs generated small neurospheres-like structures, which strongly expressed β-tubulin III. These structures were not observed when wildtype hESCs were differentiated in the presence of SU5402.

Pharmacological Inhibition of Nodal Signaling in hESCs Mimics Lefty Activity In Vitro.

In view of the complexity of generating transgenic hESC lines expressing Nodal inhibitors, we also investigated whether a specific pharmacological inhibitor of Nodal signaling, SB431542, would also lead to increased neuroectoderm specification in hESC derived EBs. Comparison of gene expression by real time qPCR in DMSO- and SB431542-treated EBs grown in CDM for 14-16 days in the presence of SB431542 showed a similar increase in the mean expression levels of Nestin, Sox3, and NGN2 to that observed in Lefty expressing EBs (FIG. 10), though there was not a significant increase in Sox1 expression levels (Student's T-test; P=0.103).

No substantial changes were observed when comparing expression of these markers in untreated and DMSO-treated cells. The addition of Activin to cultures had the opposite effects of SB431542, namely decreasing expression of the neuroectoderm markers, Sox1, Sox3, Nestin and NGN2. We also compared the time course of hESC differentiation toward neuroectoderm in the presence or in the absence of SB431542 by harvesting EBs every 4 days over a 16 days interval and analysing gene expression by RT-PCR. Inhibition of Activin/Nodal signalling by SB431542 caused a rapid down-regulation of the pluripotency marker Oct4 as compared to controls, thus apparently priming the cells for differentiation. By contrast the expression of the neuroectoderm markers Nestin, Sox3, Sox1 and NGN2 appeared to be upregulated earlier in SB431542-treated EBs than in control EBs.

These findings indicate that forced inhibition of Nodal/Activin signaling results in more rapid loss of pluripotency and acquisition of neural character by hESCs compared to spontaneous differentiation, and strongly support the conclusion that inhibition of Activin/Nodal signaling, whether by natural or pharmacological inhibitors, results in highly efficient neuroectoderm specification in vitro under defined culturing conditions in which BMP signalling is quiescent.

Effect of the PI3 Kinase Inhibitor LY294002 on Endoderm Differentiation.

hESCs were grown for 3 days in chemically defined medium PVA the presence of Activin+FGF2+BMP4 or in the presence of Activin+FGF2+BMP4+LY294002. PI3Kinase inhibition was found to increase the expression of mesoderm (Brachyury) and endoderm (Sox17, GSC, Mixl1) markers while it decreased the expression of pluripotency markers (Oct-4, Nanog, Sox2). Therefore, the addition of LY294002 improved the differentiation which was induced by the combination of Activin+FGF2+BMP4. Importantly, these results were observed only in CDM-PVA and not in CDM-BSA suggesting that BSA could inhibit the effect of LY294002 on endoderm differentiation.

The generation of fully functional cell type in culture conditions compatible with clinical applications remains a major challenge in achieving the therapeutic potential of hESCs. Here, the inventors describe humanised and chemically defined culture conditions for growing hESCs and for inducing their differentiation toward the three primary germ layers and extra-embryonic tissues. Several methods have been recently published to grow hESCs in partially defined culture conditions but most of these approaches are based on medium and extra-cellular matrices containing animal products. Two of those approaches proposed xeno-free and chemically defined media but hESCs grown in these culture conditions during a prolonged period of time can acquire genetic abnormalities. Moreover, the quantity of growth factors necessary will limit the large scale application of such approaches. These drawbacks do not concern the methods described here since hESCs cells were grown more than 90 passages in CDM/AF while maintaining a normal karyotype and a stable epigenetic status. In addition, the quantity of FGF2 and Activin required are economically compatible with their routine use. Interestingly, previous studies used different cocktails of growth factors for maintaining the pluripotent status of hESCs. FGF2 is the only common growth factor in all these culture conditions providing indication that it is the essential signalling pathway for the maintenance of pluripotence of hESCs. However, TGFβ activates the same pathway than Activin using different receptors, while it has been proposed that in the pre-gastrula mouse embryo, Wnt signalling can activate the expression of Nodal, the endogenously expressed relative of Activin. In addition, our study clearly showed that inhibition of Activin signalling in the presence of FGF2 resulted in neuroectoderm differentiation. Together, these observations confirm that Activin signalling is necessary for the maintenance of the pluripotent status of hESCs and that the function of FGF signalling in pluripotency is strictly dependent on Activin signalling.

The culture conditions described here can be used to grow and to differentiate hESCs in humanised and chemically defined culture conditions compatible with clinical applications. This approach also represents an interesting alternative to the current culture conditions available for basic studies since they reduced experimental variability and therefore they are more cost effective. The possibility to direct differentiation of hESCs into neuroectoderm, mesendoderm and extra-embryonic tissues using chemical inhibitors and cocktails of growth factors represent a first step toward the generation of fully functional cells with clinical interest. In addition, mesendoderm and neuroectoderm progenitors may have clinical value, for example for transplantation purposes. Behind these clinical applications, these methods of differentiation also represent unique in vitro models of development to study the molecular mechanisms controlling cell fate specification of pluripotent cells during the early stage of mammalian development.

TABLE 1

|  | Tra-1-60 | SSEA-3 |
|---|---|---|
| H9 SR on feeders p55 | 58% | 60% |
| H9 CDM-BSA on Fibronectin p85 | 95% | 87% |
| H9 CDM-PVA on FBSc p12 | 80% | 61% |
| hSF-6 CDM-BSA on Fibronectin p20 | 72% | 55% |
| H9 CDM-plas on HSc p17 | 97% | 95% |
| H9 CDM-huSA on HSc p25 | 94% | 87% |
| hSF-6 CDM-plas on HSc p20 | 100% | 96% |
| hSF-6 CDM-Buv on HSc p25 | 97% | 87% |

TABLE 2

| Conditions CDM | Pluripotency Oct4 | Neuro Sox2 | Meso Brachyury | Endo Sox17 |
|---|---|---|---|---|
| 0 | L | H | VL | VL |
| Activin 10 ng/ml + FGF 12 ng/ml (7 Days) | H | H | 0 | 0 |

TABLE 2-continued

| Conditions CDM | Pluripotency Oct4 | Neuro Sox2 | Meso Brachyury | Endo Sox17 |
|---|---|---|---|---|
| Activin 10 ng/ml + SU 10 μM (7 Days) | H | H | L | L |
| FGF 12 ng/ml + SB 10 μM (7 Days) | 0 | H | 0 | 0 |
| SB 10 μM + SU 10 μM | 0 | 0 | 0 | 0 |
| BMP4 50 ng/ml (7 days) | 0 | 0 | 0 | 0 |
| Acti 10 ng/ml + BMP4 50 ng/ml (7 days) | 0 | 0 | 0 | 0 |
| 0 (4 or 5 days) + BMP4 50 ng/ml (3 days) | 0 | 0 | 0 | 0 |
| 0 (4 or 5 days) + Activin 30 ng/ml + FGF 12 ng/ml (3 days) | H | H | L | L |
| 0 (4 or 5 days) + Activin 30 ng/ml + BIO 5 μM (3 days) | L | H | 0 | 0 |
| SB 10 μM + BIO 5 μM (7 days) | 0 | H | 0 | 0 |
| 0 (4 or 5 days) + Activin 30 ng/ml + SU 10 μM (3 days) | L | L | L | VL |
| BMP4 50 ng/ml + Activin 30 ng/ml (7 days) | 0 | 0 | 0 | 0 |
| SB 10 μM + BMP4 50 ng/ml + FGF2 12 ng/ml (7 days) | 0 | L | 0 | 0 |
| SB 10 μM (5 days) + BMP4 50 ng/ml + Activin 30 ng/ml (3 days) | 0 | H | 0 | 0 |
| SB 10 μM (5 days) + Acti 30 ng/ml (3 days) | 0 | H | 0 | 0 |
| SB 10 μM (5 days) + Acti 30 ng/ml + FGF 12 ng/ml (3 days) | 0 | H | 0 | 0 |
| SU 10 μM (3 days) Activin 30 ng/ml (4 days) | H | H | L | L |
| SU 10 μM (4 days) Activin 30 ng/ml (4 days) | H | H | L | L |
| SU 10 μM (5 days) Activin 30 ng/ml (4 days) | L | L | L | L |

TABLE 3

| Conditions CDM-PVA | Pluripotency Oct4 | Neuro Sox2 | Meso Brachyury | Endo Sox17 |
|---|---|---|---|---|
| Activin 10 ng/ml + FGF 12 ng/ml (7 Days) | H | H | 0 | 0 |
| Activin 10 ng/ml + SU 10 (7 Days) | H | H | L | L |
| FGF 12 ng/ml + SB 10 (7 Days) | 0 | H | 0 | 0 |
| SU 10 (3 days) Activin 30 ng/ml (4 days) | H | H | L | L |
| SU 10 (4 days) Activin 30 ng/ml (4 days) | H | H | L | L |
| SU 10 (5 days) Activin 30 ng/ml (4 days) | H | H | VL | VL |
| Activin 5 ng/ml + SU 10 (3 days) Activin 30 ng/ml (4 days) | L | L | H | H |
| Activin 5 ng/ml + SU 10 (3 days) Activin 100 ng/ml (4 days) | L | L | L | H |
| Activin 5 ng/ml + SU 10 (3 days) Activin 30 ng/ml + FGF 20 ng/ml + BMP4 10 ng/ml (4 days) | L | L | VH | VH |

TABLE 4a

Down regulated with EMP4

| Gene name | Gene symbol | Margin | p-value | q-value |
|---|---|---|---|---|
| left-right determination factor 1 | LEFTY1 | −6.56 | 1.13E−08 | 2.29E−06 |
| hypothetical protein BC012029 | LOC152573 | −5.04 | 1.53E−09 | 8.30E−07 |
| lecithin retinol acyltransferase | LRAT | −4.97 | 5.65E−08 | 5.76E−06 |
| orthodenticle homolog 2 (*Drosophila*) | OTX2 | −4.89 | 2.34E−08 | 3.52E−06 |
| hypothetical protein LOC153469 | LOC153469 | −4.72 | 3.01E−09 | 1.10E−06 |
| hypothetical protein MGC26963 | MGC26963 | −4.02 | 1.45E−09 | 8.14E−07 |
| oligodendrocyte transcription factor 3 | OLIG3 | −3.9 | 3.80E−05 | 4.15E−04 |
| thrombospondin 2 | THBS2 | −3.73 | 4.32E−10 | 6.21E−07 |
| SRY (sex determining region Y)-box 2 | SOX2 | −3.64 | 4.70E−09 | 1.39E−06 |
| ubiquitin specific protease 44 | USP44 | −3.63 | 7.28E−08 | 6.63E−06 |
| protein phosphatase 2 | PPP2R2B | −3.6 | 8.99E−09 | 1.99E−06 |
| transmembrane protein 46 | TMEM46 | −3.57 | 1.72E−05 | 2.40E−04 |
| UDP glycosyltransferase 8 | UGT8 | −3.57 | 4.50E−08 | 5.14E−06 |
| papilin | PAPLN | −3.53 | 1.34E−08 | 2.58E−06 |
| growth differentiation factor 3 | GDF3 | −3.47 | 2.55E−07 | 1.43E−05 |

TABLE 4a-continued

Down regulated with EMP4

| Gene name | Gene symbol | Margin | p-value | q-value |
|---|---|---|---|---|
| Arg/Abl-interacting protein ArgBP2 | ARGBP2 | −3.43 | 2.68E−08 | 3.86E−06 |
| forkhead box A2 (splice variant) | FOXA2 | −3.38 | 1.69E−07 | 1.11E−05 |
| Nanog homeobox | NANOG | −3.22 | 2.54E−07 | 1.43E−05 |
| hypothetical protein FLJ90231 | FLJ90231 | −3.15 | 5.16E−08 | 5.43E−06 |
| MEGF10 protein | MEGF10 | −3.14 | 1.17E−06 | 3.81E−05 |
| left-light determination factor 2 | LEFTY2 | −3.12 | 2.98E−07 | 1.56E−05 |
| dickkopf homolog 4 (Xenopus laevis) | DKK4 | −3.09 | 6.02E−07 | 2.45E−05 |
| thymus high mobility group box protein TOX | TOX | −3.03 | 4.47E−09 | 1.35E−06 |
| Kallmann syndrome 1 sequence | KAL1 | −2.98 | 5.84E−07 | 2.41E−05 |
| non-coding RNA in rhabdomyosarcoma (RMS) | NCRMS | −2.98 | 9.35E−08 | 7.61E−06 |
| Rat proto-oncogene | RET | −2.97 | 2.86E−09 | 1.08E−06 |
| nodal homolog (mouse) | NODAL | −2.93 | 6.10E−07 | 2.48E−05 |
| tissue inhibitor of metalloproteinase 4 | TIMP4 | −2.9 | 4.67E−08 | 5.18E−06 |
| importin 9 | IPO9 | −2.83 | 1.84E−07 | 1.18E−05 |
| leucine-rich repeats | LRIG1 | −2.82 | 5.72E−09 | 1.50E−06 |
| transcription factor RAM2 | RAM2 | −2.8 | 2.51E−08 | 3.67E−06 |
| secreted frizzled-related protein 2 | SFRP2 | −2.75 | 2.93E−07 | 1.55E−05 |
| potassium voltage-gated channel | KCND2 | −2.74 | 3.53E−07 | 1.75E−05 |
| nuclear factor (erythroid-derived 2)-like 3 | NFE2L3 | −2.74 | 6.16E−06 | 1.18E−04 |
| chromosome 2 open reading frame 31 | C2orf31 | −2.72 | 5.46E−08 | 5.65E−06 |
| D21S2088E | D21S2088E | −2.67 | 1.67E−06 | 4.79E−05 |
| lymphocyte-specific protein tyrosine kinase | LCK | −2.65 | 5.72E−07 | 2.38E−05 |
| chromosome 10 open reading frame 13 | C10orf13 | −2.63 | 1.53E−08 | 2.81E−06 |
| hematopoietically expressed homeobox | HHEX | −2.58 | 4.81E−07 | 2.12E−05 |
| pipecolic acid oxidase | PIPOX | −2.58 | 1.22E−09 | 7.60E−07 |
| Adenylate kinase 3 | AK3 | −2.55 | 2.07E−09 | 9.57E−07 |
| leukocyte cell derived chemotaxin 1 | LECT1 | −2.55 | 3.38E−06 | 7.75E−05 |
| carbohydrate sulfotransferase 9 | CHST9 | −2.54 | 1.92E−05 | 2.59E−04 |
| transient receptor potential cation channel | TRPC4 | −2.52 | 2.28E−08 | 3.51E−06 |
| cytochrome P450 | CYP26A1 | −2.51 | 2.76E−06 | 6.78E−05 |
| adrenergic, alpha-2A-, receptor | ADRA2A | −2.49 | 4.01E−06 | 8.73E−05 |
| ets variant gene 1 | ETV1 | −2.49 | 4.44E−06 | 9.30E−05 |
| undifferentiated embryonic cell transcription factor 1 | UTF1 | −2.47 | 1.28E−06 | 4.06E−05 |
| G protein-coupled receptor 64 | GPR64 | −2.46 | 1.55E−07 | 1.04E−05 |
| chromosome 14 open reading frame 29 | C14orf29 | −2.44 | 1.06E−07 | 8.14E−06 |
| Calcium channel | CACNA2D3 | −2.42 | 3.05E−09 | 1.10E−06 |
| CUB and zona pellucida-like domains 1 | CUZD1 | −2.4 | 2.04E−06 | 5.56E−05 |
| Kruppel-like factor 4 (gut) | KLF4 | −2.4 | 2.18E−07 | 1.31E−05 |
| Solute carrier family 1, member 6 | SLC1A6 | −2.39 | 1.01E−05 | 1.64E−04 |
| mal, T-cell differentiation protein 2 | MAL2 | −2.37 | 5.30E−06 | 1.05E−04 |
| protein tyrosine phosphatase | PTPRZ1 | −2.37 | 3.53E−07 | 1.75E−05 |
| homeo box (expressed in ES cells) 1 | HESX1 | −2.36 | 2.37E−06 | 6.12E−05 |
| secreted frizzled-related protein 1 | SFRP1 | −2.36 | 1.69E−08 | 2.97E−06 |

TABLE 4b

| Gene name | Gene symbol | Margin | p-value | q-value |
|---|---|---|---|---|
| hyaluronan and proteoglycan link protein 1 | HAPLN1 | 8.04 | 6.31E−12 | 1.24E−07 |
| gamma-aminobutyric acid (GABA) A receptor, pi | GABRP | 7.34 | 1.72E−11 | 1.24E−07 |
| heart and neural crest derivatives expressed 1 | HAND1 | 7.27 | 5.32E−11 | 2.48E−07 |
| ISL1 transcription factor | ISL1 | 6.5 | 1.32E−11 | 1.24E−07 |
| distal-less homeo box 2 | DLX2 | 6.43 | 4.27E−09 | 1.34E−06 |
| T-box 3 (ulnar mammary syndrome) | TBX3 | 6.42 | 1.20E−11 | 1.24E−07 |
| GATA binding protein 3 | GATA3 | 6.21 | 2.62E−11 | 1.51E−07 |
| endothelial PAS domain protein 1 | EPAS1 | 6.2 | 1.79E−10 | 4.51E−07 |
| lumican | LUM | 5.88 | 6.03E−11 | 2.48E−07 |
| periostin, osteoblast specific factor | POSTN | 5.83 | 1.29E−08 | 2.51E−06 |
| Inhibitor of DNA binding 4 | ID4 | 5.47 | 2.63E−10 | 4.76E−07 |
| msh homeo box homolog 2 (Drosophila) | MSX2 | 5.43 | 3.06E−09 | 1.10E−06 |
| homeo box B6 | HOXB6 | 5.19 | 2.12E−07 | 1.29E−05 |
| corticotropin releasing hormone | CRH | 5.13 | 2.16E−08 | 3.37E−06 |
| Chloride intracellular channel 5 | CLIC5 | 5.04 | 7.62E−09 | 1.78E−06 |
| transcription factor AP-2 alpha | TFAP2A | 4.98 | 9.98E−08 | 7.83E−06 |
| snail homolog 2 (Drosophila) | SNAI2 | 4.92 | 5.68E−08 | 5.76E−06 |
| transcription factor CP2-like 4 | TFCP2L4 | 4.92 | 4.94E−08 | 5.36E−06 |
| forkhead box F1 | FOXF1 | 4.84 | 1.12E−07 | 8.42E−06 |
| Hypothetical protein FLJ25477 | FLJ25477 | 4.77 | 9.93E−10 | 7.14E−07 |
| distal-less homeo box 6 | DLX6 | 4.66 | 2.20E−08 | 4.51E−07 |
| myocardin | MYOCD | 4.49 | 7.81E−10 | 6.91E−07 |
| collagen, type III, alpha 1 | COL3A1 | 4.47 | 8.03E−08 | 7.06E−06 |
| regulator of G-protein signalling 5 | RGS5 | 4.46 | 3.49E−09 | 1.22E−06 |
| synaptopodin 2 | SYNPO2 | 4.46 | 3.12E−08 | 4.18E−06 |

TABLE 4b-continued

| Gene name | Gene symbol | Margin | p-value | q-value |
|---|---|---|---|---|
| cripto, FRL-1, Glyptic family 1 | CFC1 | 4.45 | 4.93E−09 | 1.42E−06 |
| insulin-like growth factor binding protein 3 | IGFBP3 | 4.44 | 8.65E−09 | 1.93E−06 |
| regulator of G-protein signalling 13 | RGS13 | 4.42 | 3.03E−08 | 4.11E−06 |
| Noggin | NOG | 4.37 | 1.76E−07 | 1.14E−05 |
| ephrin-A1 | EFNA1 | 4.35 | 8.73E−10 | 6.91E−07 |
| angiotensin II receptor-like 1 | AGTRL1 | 4.35 | 1.24E−09 | 7.60E−07 |
| Lix1 homolog (mouse) | LIX1 | 4.3 | 1.97E−08 | 3.15E−06 |
| Deiodinase, iodothyronine, type II | DIO2 | 4.29 | 5.51E−08 | 5.68E−06 |
| msh homeo box homolog 1 (*Drosophila*) | MSX1 | 4.28 | 1.89E−07 | 1.20E−05 |
| hypothetical LOC387763 | LOC387763 | 4.25 | 2.57E−09 | 1.01E−06 |
| tripartite motif-containing 55 | TRIM55 | 4.24 | 2.51E−09 | 1.01E−06 |
| solute carrier family 40 | SLC40A1 | 4.19 | 6.15E−10 | 6.27E−07 |
| actin, alpha, cardiac muscle | ACTC | 4.16 | 9.35E−10 | 6.91E−07 |
| SRY (sex determining region Y)-box 7 | SOX7 | 4.13 | 5.04E−09 | 1.44E−06 |
| Protease, serine, 12 (neurotrypsin, motopsin) | PRSS12 | 4.09 | 2.71E−09 | 1.04E−06 |
| PTPL1-associated RhoGAP 1 | PARG1 | 4.04 | 3.96E−09 | 1.28E−06 |
| distal-less homeo box 5 | DLX5 | 4.04 | 4.90E−06 | 9.97E−05 |
| mesoderm posterior 1 | MESP1 | 4.03 | 2.19E−07 | 1.31E−05 |
| Meis1, myeloid ecotropic viral integration site 1 | MEIS1 | 4.02 | 5.19E−07 | 2.23E−05 |
| potassium channel tetramerisation | KCTD12 | 4.01 | 1.25E−07 | 9.04E−06 |
| solute carrier family 16 | SLC16A4 | 4 | 2.66E−09 | 1.03E−06 |
| GATA binding protein 5 | GATA5 | 4 | 1.93E−08 | 3.14E−06 |
| H19, imprinted maternally expressed mRNA | H19 | 3.98 | 3.55E−08 | 4.46E−06 |
| suppressor of cytokine signaling 3 | SOCS3 | 3.98 | 1.93E−09 | 9.08E−07 |
| hairy/enhancer-of-split related with YRPW motif 1 | HEY1 | 3.93 | 2.16E−09 | 9.58E−07 |
| protein kinase D1 | PRKD1 | 3.91 | 1.77E−09 | 8.97E−07 |
| keratin 7 | KRT7 | 3.91 | 4.03E−08 | 4.79E−06 |
| sema domain, immunoglobulin domain (Ig) | SEMA3C | 3.89 | 1.22E−07 | 8.90E−06 |
| transcription factor CP2-like 2 | TFCP2L2 | 3.87 | 2.08E−07 | 1.28E−05 |
| BMP and activin membrane-bound inhibitor | BAMBI | 3.86 | 1.55E−10 | 4.46E−07 |
| regulator of G-protein signalling 4 | RGS4 | 3.85 | 4.64E−08 | 5.18E−06 |
| cadherin 11, type 2, OB-cadherin (osteoblast) | CDH11 | 3.81 | 6.32E−10 | 6.27E−07 |
| KIAA0882 protein | KIAA0882 | 3.81 | 4.30E−09 | 1.34E−06 |

REFERENCES

Tam, P. P. et al Curr Opin Genet Dev 13, 393-400 (2003).
Schier, A. F. & Talbot, W. S. Annu Rev Genet 39, 561-613 (2005).
Robb, L. & Tam, P. P. Semin Cell Dev Biol 15, 543-554 (2004).
Johansson, B. M. & Wiles, M. V. Mol Cell Biol 15, 141-151 (1995).
Inman, G. J. et al Mol Pharmacol 62, 65-74 (2002).
Mohammadi, M. et al. Science 276, 955-960 (1997).
Sato, N. et al Nat Med 10, 55-63 (2004).
D'Amour, K. A. et al. Nat Biotechnol 23, 1534-1541 (2005).
Yasunaga, M. et al. Nat Biotechnol 23, 1542-1550 (2005).
Vallier, L. et al Dev Biol 275, 403-421 (2004a).
Vallier, L. et al., 2004b. Stem Cells 22, 2-11. 653
Vallier, L., et al 2005. J. Cell. Sci. 118, 4495-4509.
Pratt, T. et al., 2000. Dev. Biol. 228, 19-28.
Camus, A. et al Dev Biol 295, 743-755 (2006).
Takaoka, K. et al. Dev Cell 10, 451-459 (2006).
Xu, R. H. et al. Nat Biotechnol 20, 1261-1264 (2002).
Ying, Q. L. et al Cell 115, 281-292 (2003).
Tada, S. et al. Development 132, 4363-4374 (2005).
Kubo, A. et al. Development 131, 1651-1662 (2004).
Irizarry, R. A. et al. Nucleic Acids Res 31, e15 (2003).
Smyth, G. K. Stat Appl Genet Mol Biol 3, Article 3 (2004).
Storey, J. D. & Tibshirani, R. PNAS USA 100, 9440-9445 (2003).
Sambrook et al. 2001. Molecular Coning, 3rd ed. Cold Spring Harbour Laboratory Press.

What is claimed is:

1. A method of producing a population of ectoderm progenitor cells, comprising:
culturing human pluripotent cells in a medium supplemented with FGF2 and an activin antagonist; and
allowing said human pluripotent cells to differentiated into said progenitor cells, wherein said medium is devoid of non-human animal components.

2. The method according to claim 1, wherein the progenitor cells are neuroectoderm progenitor cells.

3. The method according to claim 2, wherein the medium is supplemented with 1 to 100 μM of the activin antagonist.

4. The method according to claim 2, wherein the medium is supplemented with 1 to 100 ng/ml of FGF2.

5. A method of producing a population of mesoderm progenitor cells or endoderm progenitor cells comprising:
culturing human pluripotent cells in a medium supplemented with activin, FGF2, BMP4, and a phosphatidyl-3-inositol kinase inhibitor, and allowing said human pluripotent cells to differentiate into said progenitor cells, wherein the medium is devoid of non-human animal components.

6. A method of producing a population of mesoderm progenitor cells or endoderm progenitor cells comprising:
(i) culturing human pluripotent cell in a medium comprising polyvinyl alcohol (PVA) and supplemented with activin and FGF2, wherein the medium is devoid of non-human components;
(ii) further culturing cells that result from step (i) in medium comprising PVA and supplemented with FGF2 antagonist and activin, wherein the medium is devoid of non-human components;
(iii) further culturing cells that result from (ii) in medium comprising PVA and supplemented with FGF2, BMP4, and activin, wherein the medium is devoid of non-human components.

7. The method according to claim 6, wherein the concentration of activin in step (ii) is less than the concentration of activin in step (i).

8. The method according to claim 6, wherein the medium in step (i) is supplemented with 5 to 20 ng/ml activin and 1 to 50 ng/ml FGF2.

9. The method according to claim 6, wherein the medium in step (ii) is supplemented with 1 to 50 μM FGF2 antagonist and 1 to 10 ng/ml activin.

10. The method according to claim 6, wherein the medium in step (iii) is supplemented with 1 to 100 ng/ml FGF2, 1 to 100 ng/ml BMP4, and 1 to 200 ng/ml activin.

11. The method according to claim 10, wherein the medium in step (iii) is supplemented with more than 50 ng/ml activin and the progenitor cells are endoderm progenitor cells.

12. The method according to claim 10, wherein the medium in step (iii) is supplemented with less than 50 ng/ml activin and the progenitor cells are mesoderm progenitor cells.

13. The method according to claim 1, wherein the medium comprises a basal defined medium, insulin, transferrin, 1-thioglycerol, and one or both of human serum albumin and PVA.

14. The method according to claim 1, further comprising isolating and/or purifying said progenitor cells.

15. The method according to claim 5, wherein the medium comprises a basal defined medium, insulin, transferrin, 1-thiolglycerol, and one or both of human serum albumin and PVA.

16. The method according to claim 5 or 6, further comprising isolating and/or purifying said progenitor cells.

17. The method according to claim 6, wherein the medium of steps (i)-(iii) comprise a basal defined medium, insulin, transferrin, and 1-thiolgycerol.

* * * * *